United States Patent
Sathaye

(10) Patent No.: US 8,185,202 B2
(45) Date of Patent: *May 22, 2012

(54) IMPLANTABLE CARDIAC DEVICE FOR REDUCED PHRENIC NERVE STIMULATION

(75) Inventor: Alok S. Sathaye, Boston, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 880 days.

This patent is subject to a terminal disclaimer.

(21) Appl. No.: 12/154,410

(22) Filed: May 22, 2008

(65) Prior Publication Data
US 2008/0294215 A1    Nov. 27, 2008

Related U.S. Application Data

(63) Continuation of application No. 11/114,569, filed on Apr. 26, 2005, now Pat. No. 7,392,086.

(51) Int. Cl.
*A61N 1/37* (2006.01)
(52) U.S. Cl. ............... 607/27; 607/9; 600/510
(58) Field of Classification Search ........... 607/9, 27; 600/510
See application file for complete search history.

(56) References Cited

U.S. PATENT DOCUMENTS

| | | |
|---|---|---|
| 3,920,005 A | 11/1975 | Gombrich et al. |
| 4,023,564 A | 5/1977 | Valiquette et al. |
| 4,340,063 A | 7/1982 | Maurer |
| 4,364,396 A | 12/1982 | Barthel |
| 4,365,636 A | 12/1982 | Barker |
| 4,458,692 A | 7/1984 | Simson |
| 4,476,869 A | 10/1984 | Bihn |
| 4,550,221 A | 10/1985 | Mabusth |
| 4,552,154 A | 11/1985 | Hartlaub |
| 4,562,841 A | 1/1986 | Brockway et al. |
| 4,573,481 A | 3/1986 | Bullara |
| 4,648,407 A | 3/1987 | Sackner |
| 4,680,708 A | 7/1987 | Ambos et al. |
| 4,686,332 A | 8/1987 | Greanias et al. |
| 4,827,935 A | 5/1989 | Geddes et al. |

(Continued)

FOREIGN PATENT DOCUMENTS

EP    0468720    1/1992

(Continued)

OTHER PUBLICATIONS

U.S. Appl. No. 11/890,668, filed Aug. 7, 2007, Sathaye et al.

(Continued)

*Primary Examiner* — Carl H Layno
*Assistant Examiner* — Jessica Sarcione
(74) *Attorney, Agent, or Firm* — Hollingsworth & Funk, LLC

(57) ABSTRACT

Methods and devices for reducing phrenic nerve stimulation of cardiac pacing systems involve delivering a pacing pulse to a ventricle of a heart. A transthoracic impedance signal is sensed, and a deviation in the signal resulting from the pacing pulse may be used to determine phrenic nerve stimulation. Methods may further involve detecting the phrenic nerve stimulation from the pacing pulse by delivering two or more pacing pulse to the ventricle of the heart, and determining a temporal relationship. A pacing vector may be selected from the two or more vectors that effects cardiac capture and reduces the phrenic nerve stimulation. A pacing voltage and/or pulse width may be selected that provides cardiac capture and reduces the phrenic nerve stimulation. In other embodiments, a pacing pulse width and a pacing voltage may be selected from a patient's strength-duration curve that effects cardiac capture and reduces the phrenic nerve stimulation.

28 Claims, 9 Drawing Sheets

U.S. PATENT DOCUMENTS

| | | |
|---|---|---|
| 4,860,766 A | 8/1989 | Sackner |
| 4,878,497 A | 11/1989 | Callaghan et al. |
| 4,928,688 A | 5/1990 | Mower |
| 4,953,551 A | 9/1990 | Mehra et al. |
| 4,979,507 A | 12/1990 | Heinz |
| 5,000,189 A | 3/1991 | Throne et al. |
| 5,033,467 A | 7/1991 | Bocchi et al. |
| 5,036,849 A | 8/1991 | Hauck et al. |
| 5,101,831 A | 4/1992 | Koyama et al. |
| 5,105,354 A | 4/1992 | Nishimura |
| 5,133,353 A | 7/1992 | Hauser |
| 5,146,918 A | 9/1992 | Kallok et al. |
| 5,170,784 A | 12/1992 | Ramon et al. |
| 5,178,156 A | 1/1993 | Takishima et al. |
| 5,179,945 A | 1/1993 | Van Hofwegen et al. |
| 5,184,615 A | 2/1993 | Nappholz et al. |
| 5,187,657 A | 2/1993 | Forbes |
| 5,203,348 A | 4/1993 | Dahl et al. |
| 5,209,229 A | 5/1993 | Gilli |
| 5,217,021 A | 6/1993 | Steinhaus et al. |
| 5,222,493 A | 6/1993 | Sholder |
| 5,230,337 A | 7/1993 | Dahl et al. |
| 5,233,983 A | 8/1993 | Markowitz |
| 5,261,400 A | 11/1993 | Bardy |
| 5,271,411 A | 12/1993 | Ripley et al. |
| 5,273,035 A | 12/1993 | Markowitz et al. |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,324,310 A | 6/1994 | Greeninger et al. |
| 5,331,966 A | 7/1994 | Bennett et al. |
| 5,331,996 A | 7/1994 | Ziehm |
| 5,333,095 A | 7/1994 | Stevenson et al. |
| 5,334,222 A | 8/1994 | Salo et al. |
| 5,335,657 A | 8/1994 | Terry, Jr. et al. |
| 5,350,410 A | 9/1994 | Kleks et al. |
| 5,353,788 A | 10/1994 | Miles |
| 5,360,442 A | 11/1994 | Dahl et al. |
| 5,366,496 A | 11/1994 | Dahl et al. |
| 5,372,606 A | 12/1994 | Lang et al. |
| 5,374,280 A | 12/1994 | den Dulk |
| 5,376,106 A | 12/1994 | Stahmann et al. |
| 5,376,476 A | 12/1994 | Eylon |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,529 A | 5/1995 | Hudrlik |
| 5,411,533 A | 5/1995 | Dubreuil et al. |
| 5,411,539 A | 5/1995 | Neisz |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,447,519 A | 9/1995 | Peterson |
| 5,468,254 A | 11/1995 | Hahn et al. |
| 5,485,851 A | 1/1996 | Erickson |
| 5,517,983 A | 5/1996 | Deighan et al. |
| 5,520,191 A | 5/1996 | Karlsson et al. |
| 5,522,860 A | 6/1996 | Molin et al. |
| 5,531,779 A | 7/1996 | Dahl et al. |
| 5,534,017 A | 7/1996 | Van Krieken et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson |
| 5,591,216 A | 1/1997 | Testerman et al. |
| 5,603,732 A | 2/1997 | Dahl et al. |
| 5,620,466 A | 4/1997 | Haefner et al. |
| 5,626,620 A | 5/1997 | Kieval et al. |
| 5,634,938 A | 6/1997 | Swanson et al. |
| 5,641,326 A | 6/1997 | Adams |
| 5,650,759 A | 7/1997 | Hittman et al. |
| 5,658,318 A | 8/1997 | Stroetmann et al. |
| 5,662,688 A | 9/1997 | Haefner et al. |
| 5,662,696 A | 9/1997 | Kroll et al. |
| 5,674,254 A | 10/1997 | Van Krieken |
| 5,683,431 A | 11/1997 | Wang |
| 5,683,434 A | 11/1997 | Archer |
| 5,697,953 A | 12/1997 | Kroll et al. |
| 5,697,956 A | 12/1997 | Bornzin |
| 5,704,365 A | 1/1998 | Albrecht et al. |
| 5,713,933 A | 2/1998 | Condie et al. |
| 5,715,812 A | 2/1998 | Deighan et al. |
| 5,718,720 A | 2/1998 | Prutchi et al. |
| 5,724,984 A | 3/1998 | Arnold et al. |
| 5,735,883 A | 4/1998 | Paul et al. |
| 5,738,102 A | 4/1998 | Lemelson |
| 5,779,645 A | 7/1998 | Olson et al. |
| 5,814,087 A | 9/1998 | Renirie |
| 5,817,027 A | 10/1998 | Arand et al. |
| 5,827,326 A | 10/1998 | Kroll et al. |
| 5,836,987 A | 11/1998 | Baumann et al. |
| 5,844,506 A | 12/1998 | Binstead |
| 5,855,593 A | 1/1999 | Olson et al. |
| 5,857,977 A | 1/1999 | Caswell et al. |
| 5,860,918 A | 1/1999 | Schradi et al. |
| 5,861,011 A | 1/1999 | Stoop |
| 5,861,013 A | 1/1999 | Peck et al. |
| 5,871,512 A | 2/1999 | Hemming et al. |
| 5,873,898 A | 2/1999 | Hemming et al. |
| 5,876,353 A | 3/1999 | Riff |
| 5,895,414 A | 4/1999 | Sanchez-Zambrano |
| 5,916,243 A | 6/1999 | Kenknight et al. |
| 5,944,680 A | 8/1999 | Christopherson et al. |
| 5,957,956 A | 9/1999 | Kroll et al. |
| 5,964,778 A | 10/1999 | Fugoso et al. |
| 5,974,340 A | 10/1999 | Kadhiresan |
| 5,987,352 A | 11/1999 | Klein et al. |
| 6,026,320 A | 2/2000 | Carlson et al. |
| 6,038,474 A | 3/2000 | Zhu et al. |
| 6,044,298 A | 3/2000 | Salo et al. |
| 6,045,513 A | 4/2000 | Stone et al. |
| 6,049,730 A | 4/2000 | Kristbjarmarson |
| 6,052,620 A | 4/2000 | Gillberg et al. |
| 6,055,454 A | 4/2000 | Heemels |
| 6,064,910 A | 5/2000 | Andersson et al. |
| 6,076,014 A | 6/2000 | Alt |
| 6,076,015 A | 6/2000 | Hartley et al. |
| 6,091,973 A | 7/2000 | Colla et al. |
| 6,101,416 A | 8/2000 | Sloman |
| 6,084,253 A | 9/2000 | Johnson et al. |
| 6,115,628 A | 9/2000 | Stadler et al. |
| 6,120,441 A | 9/2000 | Griebel |
| 6,126,611 A | 10/2000 | Bourgeois et al. |
| 6,128,534 A | 10/2000 | Park et al. |
| 6,128,535 A | 10/2000 | Maarse |
| 6,132,384 A | 10/2000 | Christopherson et al. |
| 6,134,473 A | 10/2000 | Hemming et al. |
| 6,141,581 A | 10/2000 | Olson et al. |
| 6,147,680 A | 11/2000 | Tareev |
| 6,148,230 A | 11/2000 | KenKnight |
| 6,148,234 A | 11/2000 | Struble |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,190,326 B1 | 2/2001 | McKinnon et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,227,072 B1 | 5/2001 | Ritchey et al. |
| 6,238,419 B1 | 5/2001 | Lindgren |
| 6,251,126 B1 | 6/2001 | Ottenhoff et al. |
| 6,253,102 B1 | 6/2001 | Hsu et al. |
| 6,258,039 B1 | 7/2001 | Okamoto et al. |
| 6,259,947 B1 | 7/2001 | Olson et al. |
| 6,266,554 B1 | 7/2001 | Hsu et al. |
| 6,270,457 B1 | 8/2001 | Bardy |
| 6,272,377 B1 | 8/2001 | Sweeney et al. |
| 6,275,731 B1 | 8/2001 | Zhu et al. |

| | | |
|---|---|---|
| 6,277,072 B1 | 8/2001 | Bardy |
| 6,280,380 B1 | 8/2001 | Bardy |
| 6,280,462 B1 | 8/2001 | Hauser et al. |
| 6,282,440 B1 | 8/2001 | Brodnick et al. |
| 6,285,907 B1 | 9/2001 | Kramer et al. |
| 6,299,581 B1 | 10/2001 | Rapoport et al. |
| 6,312,378 B1 | 11/2001 | Bardy |
| 6,312,388 B1 | 11/2001 | Marcovecchio et al. |
| 6,324,421 B1 | 11/2001 | Stadler et al. |
| 6,324,427 B1 | 11/2001 | Florio |
| 6,336,903 B1 | 1/2002 | Bardy |
| 6,345,201 B1 | 2/2002 | Sloman et al. |
| 6,351,669 B1 | 2/2002 | Hartley et al. |
| 6,351,673 B1 | 2/2002 | Ding et al. |
| 6,353,759 B1 | 3/2002 | Hartley et al. |
| 6,358,203 B2 | 3/2002 | Bardy |
| 6,360,127 B1 | 3/2002 | Ding et al. |
| 6,363,270 B1 | 3/2002 | Colla et al. |
| 6,363,281 B1 | 3/2002 | Zhu et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,393,316 B1 | 5/2002 | Gillberg et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,415,183 B1 | 7/2002 | Scheiner et al. |
| 6,418,340 B1 | 7/2002 | Conley et al. |
| 6,418,343 B1 | 7/2002 | Zhang et al. |
| 6,424,234 B1 | 7/2002 | Stevenson |
| 6,424,865 B1 | 7/2002 | Ding |
| 6,434,417 B1 | 8/2002 | Lovett |
| 6,434,428 B1 | 8/2002 | Sloman et al. |
| 6,438,409 B1 | 8/2002 | Malik et al. |
| 6,438,410 B2 | 8/2002 | Hsu et al. |
| 6,440,066 B1 | 8/2002 | Bardy |
| 6,449,503 B1 | 9/2002 | Hsu |
| 6,456,481 B1 | 9/2002 | Stevenson |
| 6,456,880 B1 | 9/2002 | Park et al. |
| 6,456,881 B1 | 9/2002 | Bornzin et al. |
| 6,459,929 B1 | 10/2002 | Hopper et al. |
| 6,466,820 B1 | 10/2002 | Juran et al. |
| 6,477,422 B1 | 11/2002 | Splett |
| 6,480,733 B1 | 11/2002 | Turcott |
| 6,480,734 B1 | 11/2002 | Zhang et al. |
| 6,487,443 B2 | 11/2002 | Olson et al. |
| 6,491,639 B1 | 12/2002 | Turcott |
| 6,493,586 B1 | 12/2002 | Stahmann et al. |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,542,775 B2 | 4/2003 | Ding et al. |
| 6,553,259 B2 | 4/2003 | Mouchawar et al. |
| 6,564,106 B2 | 5/2003 | Guck et al. |
| 6,567,701 B2 | 5/2003 | Vonk |
| 6,574,507 B1 | 6/2003 | Bonnet |
| 6,589,188 B1 | 7/2003 | Street et al. |
| 6,595,927 B2 | 7/2003 | Pitts-Crick |
| 6,597,951 B2 | 7/2003 | Kramer et al. |
| 6,600,949 B1 | 7/2003 | Turcott |
| 6,607,509 B2 | 8/2003 | Bobroff et al. |
| 6,611,712 B2 | 8/2003 | Spinelli et al. |
| 6,615,082 B1 | 9/2003 | Mandell |
| 6,615,083 B2 | 9/2003 | Kupper |
| 6,615,089 B1 | 9/2003 | Russie et al. |
| 6,618,619 B1 | 9/2003 | Florio et al. |
| 6,622,046 B2 | 9/2003 | Fraley et al. |
| 6,631,290 B1 | 10/2003 | Guck et al. |
| 6,640,136 B1 | 10/2003 | Helland et al. |
| 6,641,542 B2 | 11/2003 | Cho et al. |
| 6,654,637 B2 | 11/2003 | Rouw et al. |
| 6,658,293 B2 | 12/2003 | Vonk |
| 6,684,100 B1 | 1/2004 | Sweeney et al. |
| 6,690,967 B2 | 2/2004 | Meij |
| 6,701,170 B2 | 3/2004 | Stetson |
| 6,708,058 B2 | 3/2004 | Kim et al. |
| 6,725,085 B2 | 4/2004 | Schwartzman et al. |
| 6,731,973 B2 | 5/2004 | Voith |
| 6,731,983 B2 | 5/2004 | Ericksen et al. |
| 6,731,984 B2 | 5/2004 | Cho et al. |
| 6,731,985 B2 | 5/2004 | Poore et al. |
| 6,738,668 B1 | 5/2004 | Mouchawar |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,773,404 B2 | 8/2004 | Poezevera et al. |
| 6,778,860 B2 | 8/2004 | Ostroff et al. |
| 6,782,291 B1 | 8/2004 | Bornzin et al. |
| 6,788,974 B2 | 9/2004 | Bardy et al. |
| 6,830,548 B2 | 12/2004 | Bonnet et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,881,192 B1 | 4/2005 | Park |
| 6,884,218 B2 | 4/2005 | Olson et al. |
| 6,885,893 B1 | 4/2005 | Lu |
| 6,888,538 B2 | 5/2005 | Ely et al. |
| 6,889,079 B2 | 5/2005 | Bocek et al. |
| 6,890,306 B2 | 5/2005 | Poezevera |
| 6,895,274 B2 | 5/2005 | Mower |
| 6,904,315 B2 | 6/2005 | Panken et al. |
| 6,904,320 B2 | 6/2005 | Park et al. |
| 6,915,160 B2 | 7/2005 | Auricchio et al. |
| 6,915,164 B2 | 7/2005 | Bradley et al. |
| 6,917,832 B2 | 7/2005 | Hutten et al. |
| 6,925,324 B2 | 8/2005 | Shusterman |
| 6,925,330 B2 | 8/2005 | Kleine |
| 6,927,721 B2 | 8/2005 | Ostroff |
| 6,928,324 B2 | 8/2005 | Park et al. |
| 6,937,907 B2 | 8/2005 | Bardy et al. |
| 6,944,495 B2 | 9/2005 | MacAdam et al. |
| 6,944,579 B2 | 9/2005 | Shimizu |
| 6,950,702 B2 | 9/2005 | Sweeney |
| 6,950,705 B2 | 9/2005 | Bardy et al. |
| 6,952,608 B2 | 10/2005 | Ostroff |
| 6,952,610 B2 | 10/2005 | Ostroff |
| 6,954,670 B2 | 10/2005 | Ostroff |
| 6,959,214 B2 | 10/2005 | Pape et al. |
| 6,961,613 B2 | 11/2005 | Bjorling et al. |
| 6,961,619 B2 | 11/2005 | Casey |
| 6,973,350 B1 | 12/2005 | Levine et al. |
| 6,975,904 B1 | 12/2005 | Sloman |
| 6,978,178 B2 | 12/2005 | Sommer et al. |
| 6,983,264 B2 | 1/2006 | Shimizu |
| 6,988,003 B2 | 1/2006 | Bardy et al. |
| 6,993,379 B1 | 1/2006 | Kroll |
| 6,999,817 B2 | 2/2006 | Park et al. |
| 7,006,869 B2 | 2/2006 | Bradley |
| 7,025,730 B2 | 4/2006 | Cho et al. |
| 7,027,861 B2 | 4/2006 | Thompson |
| 7,027,868 B2 | 4/2006 | Rueter et al. |
| 7,027,871 B2 | 4/2006 | Burnes et al. |
| 7,031,773 B1 | 4/2006 | Levine et al. |
| 7,039,459 B2 | 5/2006 | Bardy |
| 7,039,465 B2 | 5/2006 | Bardy |
| 7,043,299 B2 | 5/2006 | Erlinger |
| 7,050,851 B2 | 5/2006 | Plombon et al. |
| 7,062,327 B2 | 6/2006 | Bradley et al. |
| 7,065,400 B2 | 6/2006 | Schechter |
| 7,065,407 B2 | 6/2006 | Bardy |
| 7,065,410 B2 | 6/2006 | Bardy et al. |
| 7,069,080 B2 | 6/2006 | Bardy |
| 7,076,296 B2 | 7/2006 | Rissmann et al. |
| 7,079,988 B2 | 7/2006 | Albera |
| 7,081,095 B2 | 7/2006 | Lynn et al. |
| 7,085,599 B2 | 8/2006 | Kim et al. |
| 7,090,682 B2 | 8/2006 | Sanders et al. |
| 7,092,754 B2 | 8/2006 | Bardy et al. |

| | | |
|---|---|---|
| 7,094,207 B1 | 8/2006 | Koh |
| 7,096,064 B2 | 8/2006 | Deno et al. |
| 7,103,404 B2 | 9/2006 | Staler et al. |
| 7,107,093 B2 | 9/2006 | Burnes |
| 7,113,823 B2 | 9/2006 | Yonce et al. |
| 7,115,097 B2 | 10/2006 | Johnson |
| 7,117,036 B2 | 10/2006 | Florio |
| 7,120,495 B2 | 10/2006 | Bardy et al. |
| 7,123,960 B2 | 10/2006 | Ding |
| 7,127,290 B2 | 10/2006 | Girouard |
| 7,129,935 B2 | 10/2006 | Mackey |
| 7,139,610 B2 | 11/2006 | Ferek-Petric |
| 7,144,586 B2 | 12/2006 | Levy et al. |
| 7,146,212 B2 | 12/2006 | Bardy et al. |
| 7,149,575 B2 | 12/2006 | Ostroff et al. |
| 7,155,278 B2 | 12/2006 | King et al. |
| 7,160,252 B2 | 1/2007 | Cho |
| 7,177,689 B2 | 2/2007 | Ternes et al. |
| 7,179,229 B1 | 2/2007 | Koh |
| 7,181,285 B2 | 2/2007 | Lindh |
| 7,184,825 B2 | 2/2007 | Kramer et al. |
| 7,184,835 B2 | 2/2007 | Kramer |
| 7,191,003 B2 | 3/2007 | Greenhut et al. |
| 7,191,004 B2 | 3/2007 | Kim et al. |
| 7,194,302 B2 | 3/2007 | Bardy et al. |
| 7,194,309 B2 | 3/2007 | Ostroff et al. |
| 7,194,313 B2 | 3/2007 | Libbus |
| 7,203,540 B2 | 4/2007 | Ding et al. |
| 7,203,542 B2 | 4/2007 | Obel |
| 7,203,543 B2 | 4/2007 | Meyer et al. |
| 7,212,862 B2 | 5/2007 | Park et al |
| 7,225,021 B1 | 5/2007 | Park et al. |
| 7,228,173 B2 | 6/2007 | Cazares |
| 7,233,821 B2 | 6/2007 | Hettrick et al. |
| 7,236,819 B2 | 6/2007 | Brockway |
| 7,242,978 B2 | 7/2007 | Cao |
| 7,242,983 B2 | 7/2007 | Frei et al. |
| 7,245,962 B2 | 7/2007 | Ciaccio et al. |
| 7,248,921 B2 | 7/2007 | Palreddy et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,286,876 B2 | 10/2007 | Yonce et al. |
| 7,299,086 B2 | 11/2007 | McCabe et al. |
| 7,299,093 B2 | 11/2007 | Zhu et al. |
| 7,308,311 B2 | 12/2007 | Sorensen |
| 7,319,900 B2 | 1/2008 | Kim et al. |
| 7,330,761 B2 | 2/2008 | Zhang |
| 7,337,000 B2 | 2/2008 | Meyer et al. |
| 7,359,749 B2 | 4/2008 | Quenet et al. |
| 7,369,889 B2 | 5/2008 | Astrom et al. |
| 7,392,086 B2 | 6/2008 | Sathaye |
| 7,426,412 B1 | 9/2008 | Schecter |
| 7,438,686 B2 | 10/2008 | Cho |
| 7,457,664 B2 | 11/2008 | Zhang et al. |
| 7,463,924 B2 | 12/2008 | Bardy et al. |
| 7,468,040 B2 | 12/2008 | Hartley |
| 7,477,932 B2 | 1/2009 | Lee |
| 7,499,751 B2 | 3/2009 | Meyer et al. |
| 7,509,170 B2 | 3/2009 | Zhang et al. |
| 7,519,423 B2 | 4/2009 | Begemann et al. |
| 7,558,628 B2 | 7/2009 | Yonce et al. |
| 7,580,741 B2 | 8/2009 | Cazares et al. |
| 7,587,240 B2 | 9/2009 | Zhang et al. |
| 7,617,002 B2 | 11/2009 | Goetz |
| 7,647,108 B2 | 1/2010 | Freeberg |
| 7,653,431 B2 | 1/2010 | Cazares et al. |
| 7,680,536 B2 | 3/2010 | Sathaye et al. |
| 7,684,861 B2 | 3/2010 | Sanders |
| 7,706,866 B2 | 4/2010 | Zhang et al. |
| 7,734,347 B2 | 6/2010 | Sathaye et al. |
| 7,738,959 B2 | 6/2010 | Manrodt et al. |
| 7,761,162 B2 | 7/2010 | Dong et al. |
| 2002/0002327 A1 | 1/2002 | Grant et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0052631 A1 | 5/2002 | Sullivan et al. |
| 2002/0082658 A1 | 6/2002 | Heinrich et al. |
| 2002/0095184 A1 | 7/2002 | Bardy et al. |
| 2002/0107544 A1 | 8/2002 | Ostroff et al. |
| 2002/0107545 A1 | 8/2002 | Rissmann et al. |
| 2002/0143264 A1 | 10/2002 | Ding et al. |
| 2003/0023175 A1 | 1/2003 | Arzbaecher et al. |
| 2003/0065365 A1 | 4/2003 | Zhu et al. |
| 2003/0083708 A1 | 5/2003 | Bradley et al. |
| 2003/0135248 A1 | 7/2003 | Stypulkowski |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0208241 A1 | 11/2003 | Bradley et al. |
| 2003/0212436 A1 | 11/2003 | Brown |
| 2004/0064162 A1 | 4/2004 | Manrodt et al. |
| 2004/0082975 A1 | 4/2004 | Meyer et al. |
| 2004/0116978 A1 | 6/2004 | Bradley |
| 2004/0172065 A1 | 9/2004 | Sih et al. |
| 2004/0215253 A1 | 10/2004 | Weinberg |
| 2004/0215277 A1 | 10/2004 | Oosterhoff et al. |
| 2004/0230229 A1 | 11/2004 | Lovett |
| 2004/0260351 A1 | 12/2004 | Holmstrom et al. |
| 2005/0004612 A1 | 1/2005 | Scholten et al. |
| 2005/0010120 A1 | 1/2005 | Jung |
| 2005/0038478 A1 | 2/2005 | Klepfer et al. |
| 2005/0043652 A1 | 2/2005 | Lovett et al. |
| 2005/0060002 A1 | 3/2005 | Zhu et al. |
| 2005/0060007 A1 | 3/2005 | Goetz |
| 2005/0065587 A1 | 3/2005 | Gryzwa |
| 2005/0085865 A1 | 4/2005 | Tehrani |
| 2005/0113710 A1 | 5/2005 | Stahmann et al. |
| 2005/0131476 A1 | 6/2005 | Kim et al. |
| 2005/0131477 A1 | 6/2005 | Meyer et al. |
| 2005/0131478 A1 | 6/2005 | Kim et al. |
| 2005/0143785 A1 | 6/2005 | Libbus |
| 2006/0069322 A1 | 3/2006 | Zhang et al. |
| 2006/0074331 A1 | 4/2006 | Kim et al. |
| 2006/0074454 A1 | 4/2006 | Freeberg |
| 2006/0111747 A1 | 5/2006 | Cazares et al. |
| 2006/0116593 A1 | 6/2006 | Zhang et al. |
| 2006/0129193 A1 | 6/2006 | Zhang |
| 2006/0129194 A1 | 6/2006 | Zhang |
| 2006/0129195 A1 | 6/2006 | Sathaye et al. |
| 2006/0129196 A1 | 6/2006 | Dong et al. |
| 2006/0129197 A1 | 6/2006 | Zhang et al. |
| 2006/0129198 A1 | 6/2006 | Zhang et al. |
| 2006/0129199 A1 | 6/2006 | Zhang et al. |
| 2006/0241711 A1 | 10/2006 | Sathaye |
| 2006/0247693 A1 | 11/2006 | Dong et al. |
| 2006/0247695 A1 | 11/2006 | Stalsberg et al. |
| 2006/0253043 A1 | 11/2006 | Zhang et al. |
| 2006/0253044 A1 | 11/2006 | Zhang et al. |
| 2007/0049974 A1 | 3/2007 | Li et al. |
| 2007/0055124 A1 | 3/2007 | Viswanathan et al. |
| 2007/0142741 A1 | 6/2007 | Berthon-Jones et al. |
| 2007/0239057 A1 | 10/2007 | Pu et al. |
| 2007/0255321 A1 | 11/2007 | Gerber et al. |
| 2008/0004665 A1 | 1/2008 | McCabe et al. |
| 2008/0009909 A1 | 1/2008 | Sathaye et al. |
| 2008/0046019 A1 | 2/2008 | Sathaye et al. |
| 2008/0071318 A1 | 3/2008 | Brooke et al. |
| 2008/0234556 A1 | 9/2008 | Brooke et al. |
| 2008/0294215 A1 | 11/2008 | Sathaye |
| 2008/0300644 A1 | 12/2008 | Sathaye |
| 2009/0030470 A1 | 1/2009 | Holmstrom |
| 2009/0043351 A1 | 2/2009 | Sathaye |
| 2009/0043352 A1 | 2/2009 | Brooke |

FOREIGN PATENT DOCUMENTS

| | | |
|---|---|---|
| EP | 0560569 | 9/1993 |
| EP | 0940155 | 9/1999 |
| EP | 1038498 | 9/2000 |
| EP | 1151718 | 11/2001 |
| EP | 1291038 | 3/2003 |
| EP | 1629863 | 3/2006 |
| WO | WO9217240 | 10/1992 |
| WO | WO9220402 | 11/1992 |
| WO | WO9904841 | 4/1999 |
| WO | WO0001438 | 1/2000 |

| WO | WO0017615 | 3/2000 |
| WO | WO0240097 | 5/2002 |
| WO | WO0247761 | 6/2002 |
| WO | WO02087696 | 11/2002 |
| WO | WO03003905 | 1/2003 |
| WO | WO03028550 | 4/2003 |
| WO | WO2004026398 | 4/2004 |
| WO | WO2004091720 | 10/2004 |
| WO | WO2005058412 | 6/2005 |
| WO | WO2005089865 | 9/2005 |
| WO | WO2006065707 | 6/2006 |
| WO | WO2007087025 | 8/2007 |
| WO | WO2008005270 | 1/2008 |
| WO | WO2009020639 | 2/2009 |

OTHER PUBLICATIONS

U.S. Appl. No. 11/116,525, filed Apr. 28, 2005, Meyer et al.
U.S. Appl. No. 11/116,544, filed Apr. 28, 2005, Meyer et al.
U.S. Appl. No. 11/116,558, filed Apr. 28, 2005, Dong et al.
U.S. Appl. No. 11/116,565, filed Apr. 28, 2005, Stalsberg et al.
U.S. Appl. No. 11/116,578, filed Apr. 28, 2005, Stalsberg et al.
U.S. Appl. No. 12/154, 411, filed May 22, 2008, Sathaye.
U.S. Appl. No. 12/220,496, filed Jul. 24, 2008, Brooke.
Office Action dated Nov. 3, 2009 from U.S. Appl. No. 11/520,879, 8 pages.
Office Action Response dated Dec. 2, 2009 from U.S. Appl. No. 11/520,879, 7 pages.
Office Action dated Mar. 10, 2010 from U.S. Appl. No. 11/520,879, 15 pages.
Office Action dated Apr. 17, 2007 from U.S. Appl. No. 11/114,569, 11 pages.
Office Action Response dated Aug. 17, 2007 from U.S. Appl. No. 11/114,569, 9 pages.
Office Action dated Nov. 14, 2007 from U.S. Appl. No. 11/114,569, 13 pages.
Office Action Response dated Jan. 14, 2008 from U.S. Appl. No. 11/114,569, 8 pages.
Notice of Allowance dated Feb. 14, 2008 from U.S. Appl. No. 11/114,569, 4 pages.
Office Action dated Nov. 9, 2007 from U.S. Appl. No. 10/955,393, 13 pages.
Office Action Response dated Apr. 21, 2008 from U.S. Appl. No. 10/955,393, 12 pages.
Office Action dated Jul. 31, 2008 from U.S. Appl. No. 10/955,393, 8 pages.
Office Action Response dated Dec. 22, 2008 from U.S. Appl. No. 10/955,393, 9 pages.
Office Action dated Mar. 20, 2009 from U.S. Appl. No. 10/955,393, 10 pages.
Office Action Response dated Jun. 9, 2009 from U.S. Appl. No. 10/955,393, 10 pages.
Notice of Allowance dated Sep. 2, 2009 from U.S. Appl. No. 10/955,393, 4 pages.
International Search Report and Written Opinion dated Dec. 12, 2008 from PCT Application No. PCT/US2008/009488, 14 pages.
International Preliminary Report on Patentability dated Feb. 18, 2010 from PCT Application No. PCT/US2008/009488, 7 pages.
Acar et al., SVD-based on-line exercise ECG signal orthogonalization, IEEE Transactions on Biomedical Engineering, vol. 46, No. 3, Mar. 1999. Abstract only.
Ajilore et al., Nightcap: Laboratory and home-based evaluation of a portable sleep monitor, 32 Psychophysiology, 32-98, 1995. Abstract only.
Belouchrani et al., Blind Source Separation Based on Time-Frequency Signal Representations, IEEE Transactions on Signal Processing, vol. 46, No. 11, pp. 2888-2897, Nov. 1998.
Cohen et al. Capture Management Efficacy in children and young adults with endocardial and unipolar epicardial systems, Europace, vol. 6, pp. 248-255, 2004.
Comon, Independent component analysis, A new concept?, Signal Processing, vol. 36, No. 3, pp. 287-314, Apr. 1994.

Gallois et al., Multi-Channel Analysis of the EEG Signals and Statistic Particularities for Epileptic Seizure Forecast, Second Joint EMBS/BMES Conference, pp. 208-215, Oct. 23-26, 2002.
Gradaus et al., Nonthoracotomy Implantable Cardioverter Defibrillator Placement in Children: Use of a Subcutaneous Array Leads and Abdominally Placed Implantable Cardioverter Defibrillators in Children, Journal of Cardiovascular Electrophysiology, vol. 12, No. 3, pp. 356-360, Mar. 2001.
Hartz et al., New Approach to Defibrillator Insertion, Journal of Thoracic Cardiovascular Surgery, vol. 97, pp. 920-922, 1989.
Hyveärinen et al., Independent Component Analysis: A Tutorial, Helsinski University of Technology, Apr. 1999.
Kolettis et al., Submammary Implantation of a Cardioverter-Defibrillator with a Nonthoractomy Lead System, American Heart Journal, vol. 126, pp. 1222-1223, Nov. 1993.
Krahn et al., Recurrent syncope. Experience with an implantable loop record, Cardiol. Clin., vol. 15(2), pp. 316-326, May 1997.
Leng et al., "Lead Configuration for Defibrillator Implantation in a Patient with Congenital Heart Disease and a Mechanical Prosthetic Tricuspid Valve", PACE, vol. 24, No. 8, pp. 1291-1292, Aug. 2001.
Park et al., Use of an Implantable Cardioverter Defibrillator in an Eight-Month-Old Infant with Ventricular Fibrillation Arising from a Myocardial Fibroma, PACE, vol. 22, No. 1, pp. 138-139, Jan. 1999.
Rieta, et al., Atrial Activity Extraction Based on Blind Source Separation as an Alternative to QRST Cancellation for Atrial Fibrillation Analysis, Computers in Cardiology, vol. 27, pp. 69-72, 2000.
Schuder et al., Experimental Ventricular Defibrillation with an Automatic and Completely Implanted System, Trans. American Society Artif. Int. Organs, vol. 16, pp. 207-212, 1970.
Schuder et al., Transthoracic Ventricular Defibrillation in the Dog with Truncated and Untruncated Exponential Stimuli, IEEE Transitions on Bio-Medical Engineering, vol. BME-18, No. 6, pp. 410-415, Nov. 1971.
Schuder et al., Ventricular Defibrillation in the Dog Using Implanted and Partially Implanted Electrode Systems, American Journal of Cardiology, vol. 33, pp. 243-247, Feb. 1974.
Smits et al., Defibrillation Threshold (DFT) Model of a Fully Subcutaneous ICD System, Europace Supplements, vol. 2, Jun. 2001 at column 778, p. B83.
Splett et al. "Determination of Pacing Capture in Implantable Defibrillators: Benefit of Evoked Response Detection Using RV Coil to Can Vector," PACE, vol. 23, 2000, pp. 1645-1650.
Stirbis et al., Optimizing of the Shape of Implanted Artificial Pacemakers, Kaunas Medical Institute, Translated from Meditsinskaya Tekhnika, No. 6, pp. 25-27, 1986.
Verrier et al., Sleep, dreams, and sudden death: the case for sleep as an autonomic stress test for the heart, 31 Cardiovascular Research 181-211, 1996.
Verrier et al., Sleep Related Cardiovascular Risk: New Home-Based Monitoring Technology for Improved Diagnosis and Therapy, 2 A.N. E. 158-175, 1997.
Waldemark et al., Detection of Apnea using Short Window FFT Technique and Artificial Neural Network, 3390 SPIE International Society for Optical Engineering 122-133, 1998. Partial article.
Zarzoso et al., Blind Separation of Independent Sources for Virtually Any Source Probability Density Function, IEEE, Transactions on Signal Processing, vol. 47, No. 9, pp. 2419-2432, Sep. 1999.
Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.
Office Action Response dated May 19, 2010 from U.S. Appl. No. 11/520,879, 13 pages.
Office Action dated Sep. 24, 2010 from U.S. Appl No. 11/890,668, 9 pages.
Office Action Response submitted Oct. 12, 2010 for U.S. Appl. No. 11/890,668, 7 pages.
Office Action dated Dec. 20, 2010 from U.S. Appl. No. 11/890,668, 12 pages.
Interview Summary dated Oct. 25, 2010 for U.S. Appl. No. 11/520,879, 4 pages.
Office Action Response submitted Nov. 1, 2010 for U.S. Appl. No. 11/520,879, 10 pages.

File history for U.S. Appl. No. 12/368,828.
File history for U.S. Appl. No. 11/520,879.
File history for U.S. Appl. No. 11/890,668.
Office Action dated May 13, 2011 from Australian Application No. 2008284265, 3 pages.

File history for EP Application No. 08795112.5 as retrieved from the European Patent Office electronic file system on Jul. 18, 2011, 140 pages.
File history for U.S. Appl. No. 12/154,411.
File history for U.S. Appl. No. 12/220,496.

IMPLANTABLE CARDIAC DEVICE FOR REDUCED PHRENIC NERVE STIMULATION

RELATED APPLICATIONS

This application is a continuation of U.S. application Ser. No. 11/114,569 filed on Apr. 26, 2005 now U.S. Pat. No. 7,392,086, which is hereby incorporated herein by reference.

FIELD OF THE INVENTION

The present invention relates generally to implantable medical devices and, more particularly, to devices and methods that reduce phrenic nerve stimulation from cardiac pacing systems.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias.

Cardiac rhythm management systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

SUMMARY OF THE INVENTION

The present invention involves various methods and devices for reducing phrenic nerve stimulation of cardiac pacing systems. Methods of cardiac pacing, in accordance with the present invention, involve delivering a pacing pulse to one or multiple ventricles of a heart using one of a plurality of vectors. A transthoracic impedance signal is sensed, and a deviation in the transthoracic impedance signal may be detected following the delivery of the pacing pulse. The presence of phrenic nerve stimulation resulting from the pacing pulse may be detected based on the deviation in the transthoracic impedance signal.

Methods of cardiac pacing, in accordance with the present invention, may further involve detecting phrenic nerve stimulation from the pacing pulse by delivering two or more pacing pulse to the ventricle of the heart, and determining a temporal relationship between the transthoracic impedance signal and the two or more pacing pulses. A pacing vector may be selected from the two or more vectors that effects cardiac capture and reduces the phrenic nerve stimulation.

Embodiments of methods in accordance with the present invention involve selecting a pacing voltage and/or pulse width that provides for cardiac capture and reduces the phrenic nerve stimulation. The transthoracic impedance signal may be evaluated for an inspiration event within an evaluation window, such as a window defined by the pacing pulse and about 500 milliseconds following the pacing pulse. In other embodiments, a pacing pulse width and a pacing voltage may be selected from a patient's strength-duration curve that effects cardiac capture and reduces the phrenic nerve stimulation.

Other embodiments of methods in accordance with the present invention involve transmitting information associated with the sensed cardiac signal and the sensed transthoracic impedance signal to a patient-external device. Pacing signal information may be received from the patient-external device. The pacing pulse may be altered based on the received pacing signal information.

Further embodiments in accordance with the present invention are directed to medical devices having two or more electrodes electrically coupled to a heart. A pulse delivery circuit may be configured to deliver a pacing pulse to a heart using the electrodes. A transthoracic impedance sensor may be provided by the device and configured to sense a transthoracic impedance signal. A control circuit may be coupled to the sensing circuit and the transthoracic impedance sensor, the control circuit configured to determine the presence of phrenic nerve stimulation resulting from the pacing pulse based on a deviation in the transthoracic impedance signal.

Other embodiments of devices in accordance with the present invention have the control circuit configured to provide pacing pulse parameters to the pulse delivery circuit, reducing phrenic nerve stimulation while maintaining cardiac capture. The control circuit may be configured to determine one or more pacing pulse parameters that reduce phrenic nerve stimulation while maintaining cardiac capture. A signal processor may be provided in a patient-external device or system, the signal processor and the control circuit coupled to respective communication devices to facilitate wireless communication between the signal processor and the control circuit. For example, the signal processor may be provided in a network server system, and coupled to communication devices to facilitate wireless communication between the signal processor and the control circuit. The control circuit may further be configured to select a pacing vector that reduces the phrenic nerve stimulation while maintaining cardiac capture.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
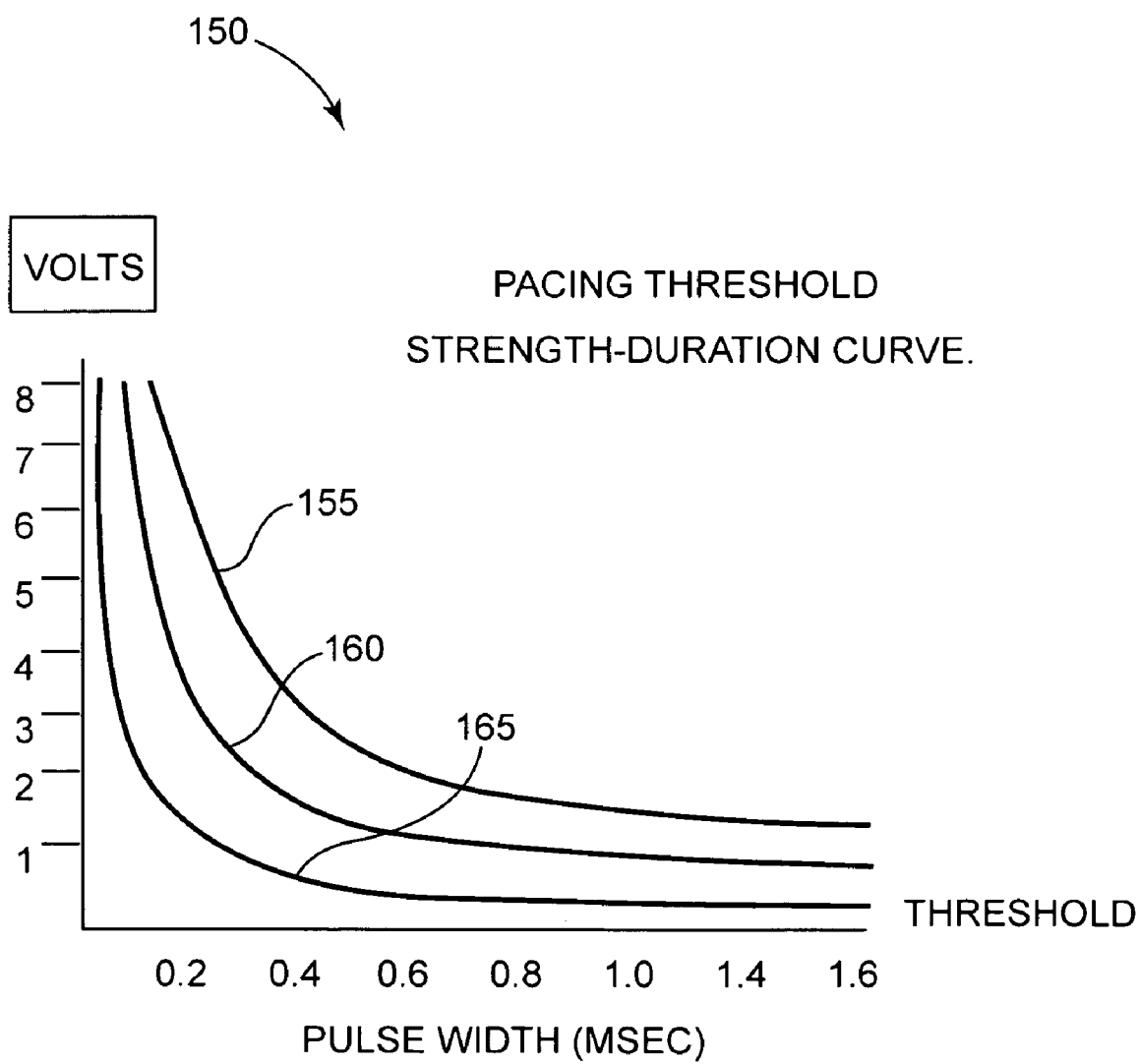
FIG. 1A is a graph illustrating examples of strength-duration curves.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

A wide variety of implantable cardiac monitoring and/or stimulation devices may be configured to implement phrenic nerve stimulation avoidance methodologies of the present invention. A non-limiting, representative list of such devices includes cardiac monitors, pacemakers, cardiovertors, defibrillators, resynchronizers, and other cardiac monitoring and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Embodiments of the present invention may be implemented in the context of a wide variety of cardiac devices, such as those listed above, and are referred to herein generally as patient-internal medical devices (PIMD) for convenience. A PIMD implemented in accordance with the present invention may incorporate one or more of the electrode types identified above and/or combinations thereof.

When a pace pulse produces a contraction in the heart tissue, the electrical cardiac signal preceding the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold provides efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

Capture may be verified by detecting if a cardiac signal following a pace pulse indicates a captured response. However, the captured response must be discerned from other responses, including the superimposed residual post pace polarization without capture, intrinsic beats, and fusion/pseudofusion beats.

Bi-ventricular pacing provides therapy options for patients suffering from heart failure. However, new challenges have been presented by placement of the left-ventricular lead via the coronary sinus in bi-ventricular pacing systems. Due to the proximity of the coronary veins to the phrenic nerve, left ventricular pacing may result in phrenic nerve stimulation. Phrenic nerve stimulation from cardiac pacing may cause the patient to exhibit uncomfortable breathing patterns timed with the left-ventricular pace. Bi-ventricular pacing PIMDs may also incorporate transthoracic impedance sensors, which provide a signal that may be used to determine information about the patient's breathing.

A patient's inspiration is associated with increasing transthoracic impedance, and expiration is associated with decreasing transthoracic impedance. Abnormal breathing patterns are detectable using breathing information inferred from a transthoracic impedance signal. In accordance with the present invention, evaluation of the transthoracic impedance signal following ventricular stimulation may be used to determine if the ventricular stimulation resulted in phrenic nerve stimulation. For example, by evaluating the transthoracic impedance signal following a ventricular pacing to determine phrenic nerve stimulation, the PIMD, which typically includes an automatic capture verification feature, can select a pacing vector, pacing voltage, pacing pulse width, or other pacing parameters, to reduce phrenic nerve stimulation while effecting capture.

Phrenic nerve stimulation, resulting in diaphragm stimulation and rapid changes in the breathing pattern, may be detected by evaluating the transthoracic impedance signal. For example, the transthoracic impedance signal may be evaluated within a time window following pacing pulse delivery, such as a window defined between a pacing pulse and about 500 milliseconds after the pacing pulse. If the transthoracic impedance signal exhibits a breathing event associated with the pace pulse, it may be assumed that the pace pulse is causing the breathing event, implying phrenic nerve stimulation. An example of such a breathing event is inspiration and/or expiration corresponding to the timing of the pace pulse, and/or a change in inspiration and/or expiration superimposed over the normal breathing pattern, where the change corresponds with the pace pulse timing.

Mitigating phrenic nerve stimulation may be accomplished several ways in accordance with the present invention. In one embodiment, during a threshold test using a particular pacing vector, phrenic nerve stimulation may be sensed using the transthoracic impedance signal. The device may change pacing vectors after detecting phrenic nerve stimulation, and attempt to find a vector that minimizes the phrenic nerve stimulation to the pace pulses. For example, a PIMD may detect phrenic nerve stimulation when using a unipolar pace vector, and attempt pacing using an extended bipolar vector to mitigate the phrenic nerve stimulation. A threshold test may then be attempted with the extended bipolar vector to determine if it effects capture and reduces phrenic nerve stimulation.

A PIMD may perform threshold tests using all available vectors, and select the best vector in terms of both desirable energy levels and reduced phrenic nerve stimulation. A search for a useful pacing vector, pacing amplitude, pacing pulse width, or other pacing parameters may be activated in either a command mode or an ambulatory mode. In a command mode, a physician may enable the test during follow-up examinations, or during remote follow-up using an advanced patient management (APM) system, as will be described in more detail below.

In an ambulatory mode, upon detection of phrenic nerve stimulation, a PIMD may select pacing parameters, such as pacing vector, pacing level, or the like, while effecting capture, such as by using capture threshold testing. The PIMD may also send an alert to a patient-external device prompting re-programming or other action.

In another embodiment in accordance with the present invention, a PIMD in ambulatory mode may incorporate automatic capture verification. The PIMD may incorporate the ability to determine a patient's strength-duration curve and/or use a programmed strength-duration curve to select one or more parameters. The PIMD, upon sensing phrenic nerve stimulation, may select another pacing voltage and pulse width on the patient's strength-duration curve that reduces or eliminates phrenic nerve stimulation. FIG. 1A is a graph 150 illustrating examples of strength-duration curves 155, 160, and 165. The graph 150 includes pulse voltage on the ordinate and pulse width on the abscissa. The curves 155, 160, and 165 may be used to select a combination of voltage and pulse width.

Other embodiments in accordance with the present invention provide PIMDs that automatically reduce phrenic nerve stimulation by selecting pacing vectors, pacing amplitudes, pacing pulse widths, or other pacing parameters when phrenic nerve stimulation is detected from a transthoracic impedance signal. This ensures that patients experience reduced breathing disruption and/or discomfort. Detection of phrenic nerve stimulation from the transthoracic impedance signal may be accomplished by determining an association between the pacing signal and a patients breathing inferred from the transthoracic impedance signal.

Figure 1B:
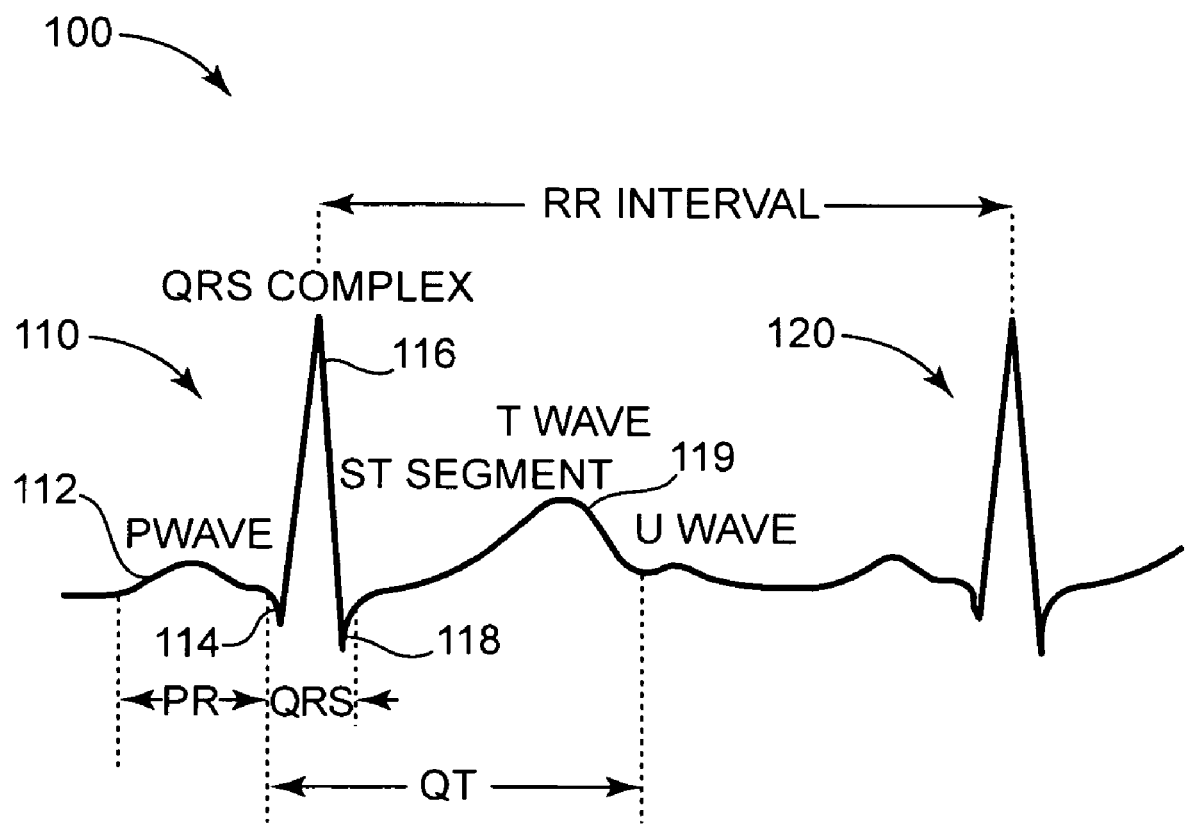
FIG. 1B is a pictorial diagram of an electrocardiogram for two consecutive heartbeats.

The relationship between a patients breathing, heartbeat (captured responses, non-captured responses, and intrinsic beats), and pacing may be determined using signals generated by and sensed using a PIMD. For example, an electrocardiogram (ECG) or electrogram (EGM) waveform describes the electrical activity of a patient's heart, where typically ECG refers to waveforms sensed from surface electrodes and EGM refers to waveforms sensed patient-internally. The graph in FIG. 1B illustrates an example of an EGM waveform 100 that describes the activation sequence of a patient's heart as recorded, for example, by a bi-polar cardiac sensing electrode. FIG. 1B is a magnified view of a first heartbeat 110, and a second heartbeat 120 of the EGM waveform 100. For purposes herein, the term heartbeat will be synonymous with cardiac cycle.

Referring to the first heartbeat 110, the portion of the EGM waveform representing depolarization of the atrial muscle fibers is referred to as a P-wave 112. Depolarization of the ventricular muscle fibers is collectively represented by a Q 114, R 116, and S 118 waves of the EGM waveform 100, typically referred to as the QRS complex, which is a well-known morphologic feature of electrocardiograms. Finally, the portion of the waveform representing repolarization of the ventricular muscle fibers is known as a T wave 119. Between contractions, the EGM waveform returns to an isopotential level.

In general, the quality of the electrocardiogram sensed from one pair of electrodes of a PIMD depends on the orientation of the electrodes with respect to the depolarization wavefront produced by the heart. The signal sensed on an electrode bi-pole is the projection of the EGM vector in the direction of the bi-pole. The sensed EGM waveform 100 illustrated in FIG. 1BA is typical of a far-field EGM signal, effectively a superposition of all the depolarizations occurring within the heart that result in contraction.

The EGM waveform 100 may also be obtained indirectly, such as by using a signal separation methodology. Signal separation methodologies, such as blind source separation (BSS), are able to separate signals from individual sources that are mixed together into a composite signal. The main principle of signal separation works on the premise that spatially distributed electrodes collect components of a signal from a common origin (e.g., the heart) with the result that these components may be strongly correlated to each other. In addition, these components may also be weakly correlated to components of another origin (e.g., noise).

A signal separation algorithm may be implemented to separate these components according to their sources and produce one or more cardiac signal vectors associated with all or a portion of one or more cardiac activation sequences based on the source separation. Cardiac activation sequence monitoring and/or tracking algorithms that exploit the strong correlation of signals from a common origin (the heart) across spatially distributed electrodes have been described further in commonly assigned U.S. patent application Ser. No. 10/955,397 filed Sep. 30, 2004, which is hereby incorporated herein by reference. Phrenic nerve avoidance algorithms in accordance with the present invention may preferably select vectors that effect capture of a patient's heart while avoiding unwanted phrenic nerve stimulation.

Figure 2A:
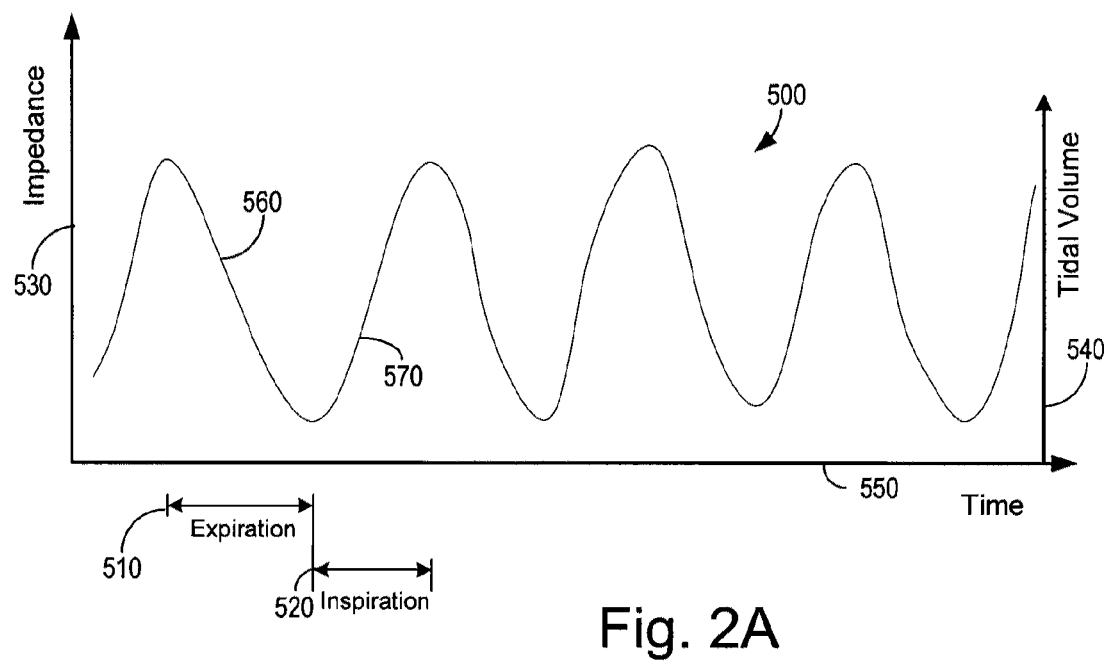
FIG. 2A is a graph of a normal respiration signal measured by a transthoracic impedance sensor that may be utilized for monitoring, diagnosis and/or therapy in accordance with embodiments of the invention.

A transthoracic impedance sensor provides another signal to the PIMD that may be analyzed to determine several events/features related to both breathing and other events. Referring now to FIG. 2A, an impedance signal 500 is illustrated. Transthoracic impedance is used in accordance with the present invention to detect phrenic nerve stimulation, and may also be useful for detecting sleep-state and other indirect measurements, such as seizures and breathing disorders. The impedance signal 500 may be developed, for example, from an impedance sense electrode in combination with an ITCS device. The impedance signal 500 is proportional to the transthoracic impedance, illustrated as an Impedance 530 on the abscissa of the left side of the graph in FIG. 2A.

The impedance 530 increases during any respiratory inspiration 520 and decreases during any respiratory expiration 510. The impedance signal 500 is also proportional to the amount of air inhaled, denoted by a tidal volume 540, illustrated on the abscissa of the right side of the graph in FIG. 2A. The variations in impedance during respiration, identifiable as the peak-to-peak variation of the impedance signal 500, may be used to determine the respiration tidal volume 540. Tidal volume 540 corresponds to the volume of air moved in a breath, one cycle of expiration 510 and inspiration 520. A minute ventilation may also be determined, corresponding to the amount of air moved per a minute of time 550 illustrated on the ordinate of the graph in FIG. 2A.

Figure 2B:
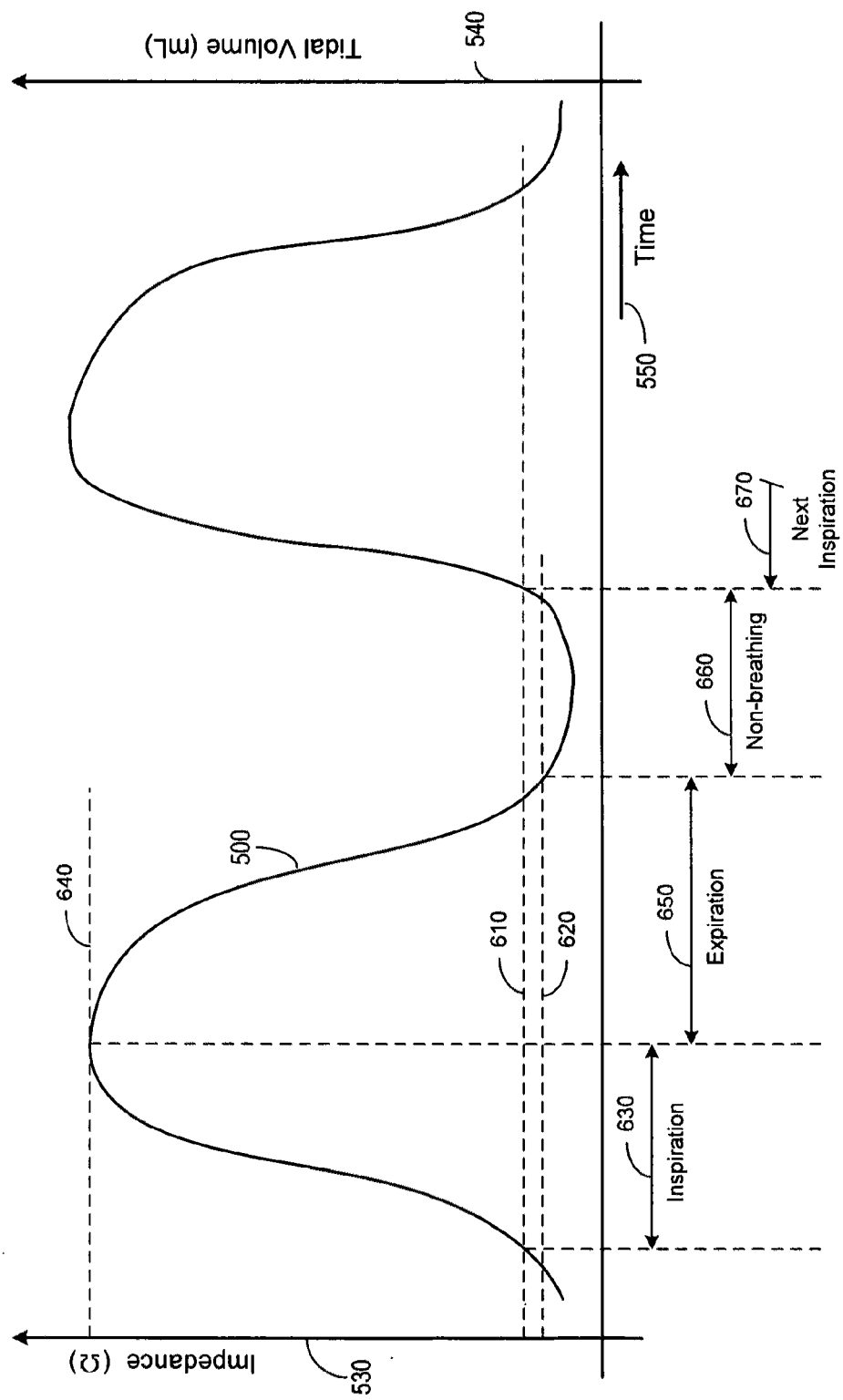
FIG. 2B is a respiration signal graph illustrating respiration intervals used for disordered breathing detection according to embodiments of the invention.
Figure 3:
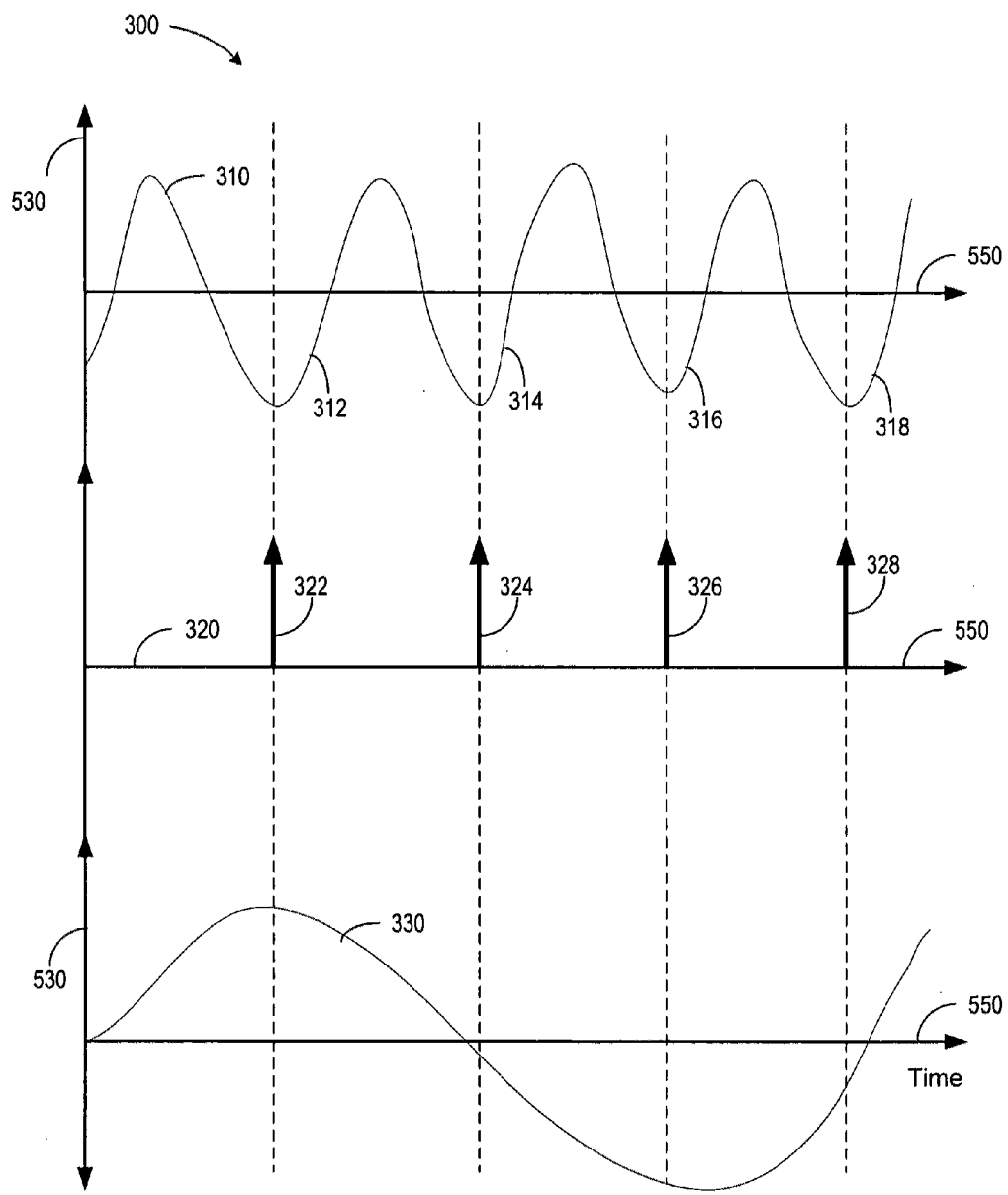
FIG. 3 is a transthoracic impedance graph illustrating detection of phrenic nerve stimulation in accordance with embodiments of the invention.

FIGS. 2A, 2B, and 3 are graphs of transthoracic impedance and tidal volume, similar to FIG. 2A previously described. As in FIG. 2A, FIGS. 2B and 3, illustrate the impedance signal 500 proportional to the transthoracic impedance, again illustrated as Impedance 530 on the abscissa of the left side of the graphs in FIGS. 2A, 2B, and 3. The impedance 530 increases during any respiratory inspiration 520 and decreases during any respiratory expiration 510. As before, the impedance signal 500 is also proportional to the amount of air inhaled, denoted the tidal volume 540, illustrated on the abscissa of the right side of the graph in FIGS. 2A, 2B, and 3. The magnitude of variations in impedance and tidal volume during respiration are identifiable as the peak-to-peak variation of the impedance signal 500.

FIG. 2B illustrates respiration intervals used for breathing detection useful in accordance with embodiments of the invention. Respiration intervals may be used to detect disordered breathing, as well as provide other sleep-state and breathing information. Detection of disordered breathing may involve defining and examining a number of respiratory cycle intervals. A respiration cycle is divided into an inspiration period corresponding to the patient inhaling, an expiration period, corresponding to the patient exhaling, and a non-breathing period occurring between inhaling and exhaling. Respiration intervals are established using an inspiration threshold 610 and an expiration threshold 620. The inspiration threshold 610 marks the beginning of an inspiration period 630 and is determined by the transthoracic impedance signal 500 rising above the inspiration threshold 610. The inspiration period 630 ends when the transthoracic impedance signal 500 is a maximum 640. The maximum transthoracic impedance signal 640 corresponds to both the end of the inspiration interval 630 and the beginning of an expiration interval 650. The expiration interval 650 continues until the transthoracic impedance 500 falls below an expiration threshold 620. A non-breathing interval 660 starts from the end of the expiration period 650 and continues until the beginning of a next inspiration period 670.

FIG. 3 is a graph 300 illustrating detection of phrenic nerve stimulation in accordance with embodiments of the invention. A transthoracic impedance signal 310 and a transthoracic impedance signal 330 are shown with respect to a cardiac pace signal 320. The cardiac pace signal 320 is illustrated as having a first pace 322, a second pace 324, a third pace 326, and a fourth pace 328. The paces 322, 324, 326 and 328 correspond to inspiration events 312, 314, 316, and 318 respectively of the transthoracic impedance signal 310. The paces 322, 324, 326 and 328 do not perceptively correspond to any features of the transthoracic impedance signal 330 in this illustration.

Although the inspiration events 312, 314, 316, and 318 are illustrated to correspond to inspiration events of complete breathing cycles for illustrative purposes, the paces 322, 324, 326 and 328 may correspond to other features of the transthoracic impedance signal 310. For example, the inspiration events 312, 314, 316, and 318 may correspond to expiration events of complete breathing cycles, or partial breathing events, such as spasms, superimposed on breathing cycles with periods that do not correspond to the pacing rate without departing from the scope of the present invention.

Figure 4:
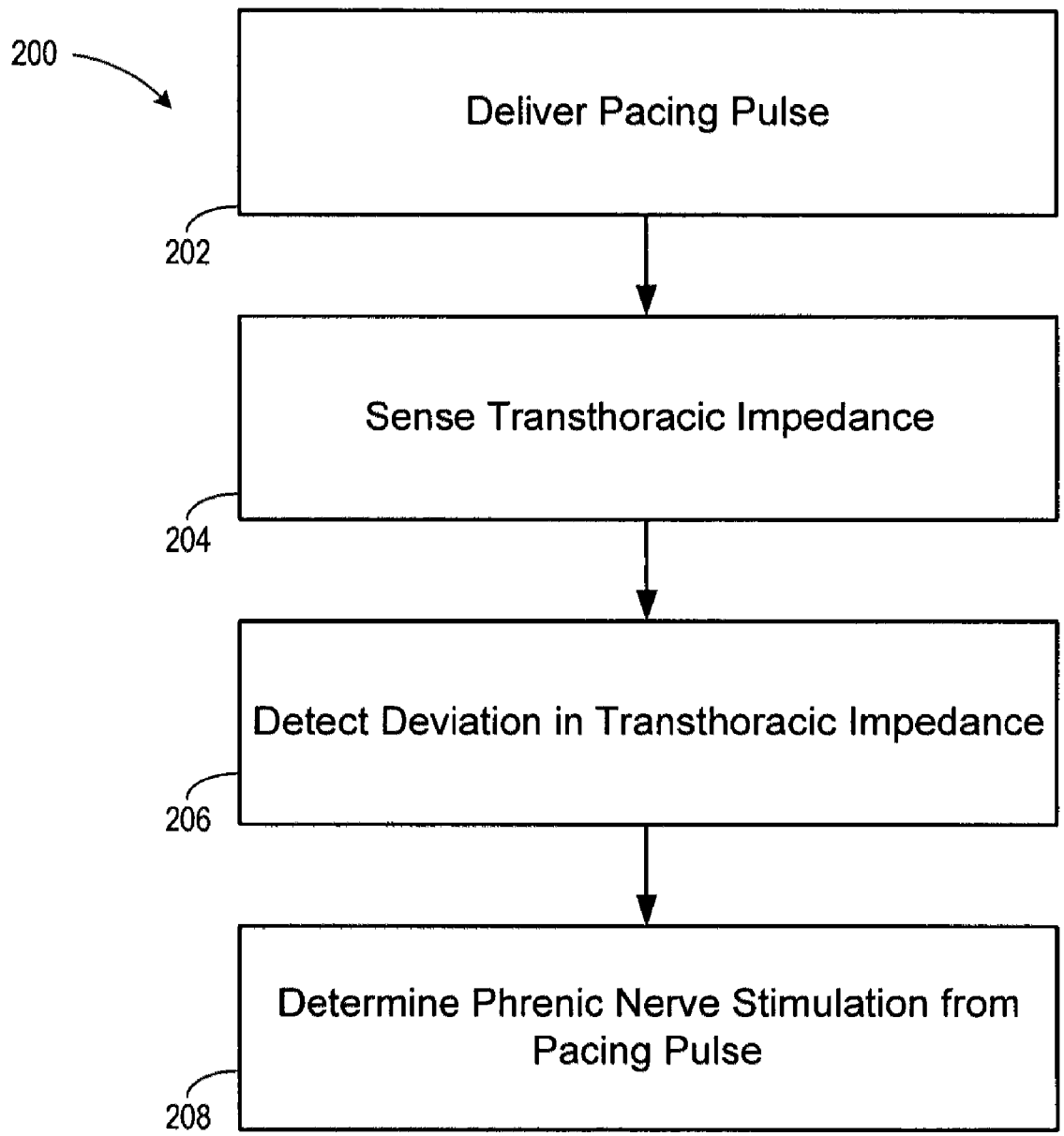
FIG. 4 is a flow chart of a method of reducing phrenic nerve stimulation in accordance with embodiments of the present invention.

FIG. 4 is a flow chart of a method 200 of determining phrenic nerve stimulation in accordance with embodiments of the present invention. Pacing pulses 200 are delivered to a patient's heart. A transthoracic impedance signal 204 is sensed. A deviation 206 of the transthoracic impedance signal 204 is detected that corresponds to the pacing pulses 202. Phrenic nerve stimulation 208 is determined from the deviation 206.

For example, pacing pulses 200 may be delivered to the patient's heart using a first vector, at a first pacing amplitude and rate. The transthoracic impedance signal 204 may exhibit the deviation 206 as a small spasm signal superimposed over the transthoracic impedance signal 204 variation due to breathing. The transthoracic impedance signal 204 may be filtered to detect the deviation 206, such as by using a bandpass filter centered at the first pacing rate.

If phrenic nerve stimulation 208 is detected, a PIMD in accordance with the present invention may alter one or more parameters to reduce the phrenic nerve stimulation. For example, the PIMD may change vectors searching for a vector that reduces the phrenic nerve stimulation. The PIMD may alter one or more of vector, amplitude, pulse width, or other parameter to reduce the phrenic nerve stimulation. It may be desirable to verify phrenic nerve stimulation for a given vector, such as by providing an extra pace during the cardiac refractory period, to determine phrenic nerve response to the extra pace independent of cardiac motion.

Figure 5:
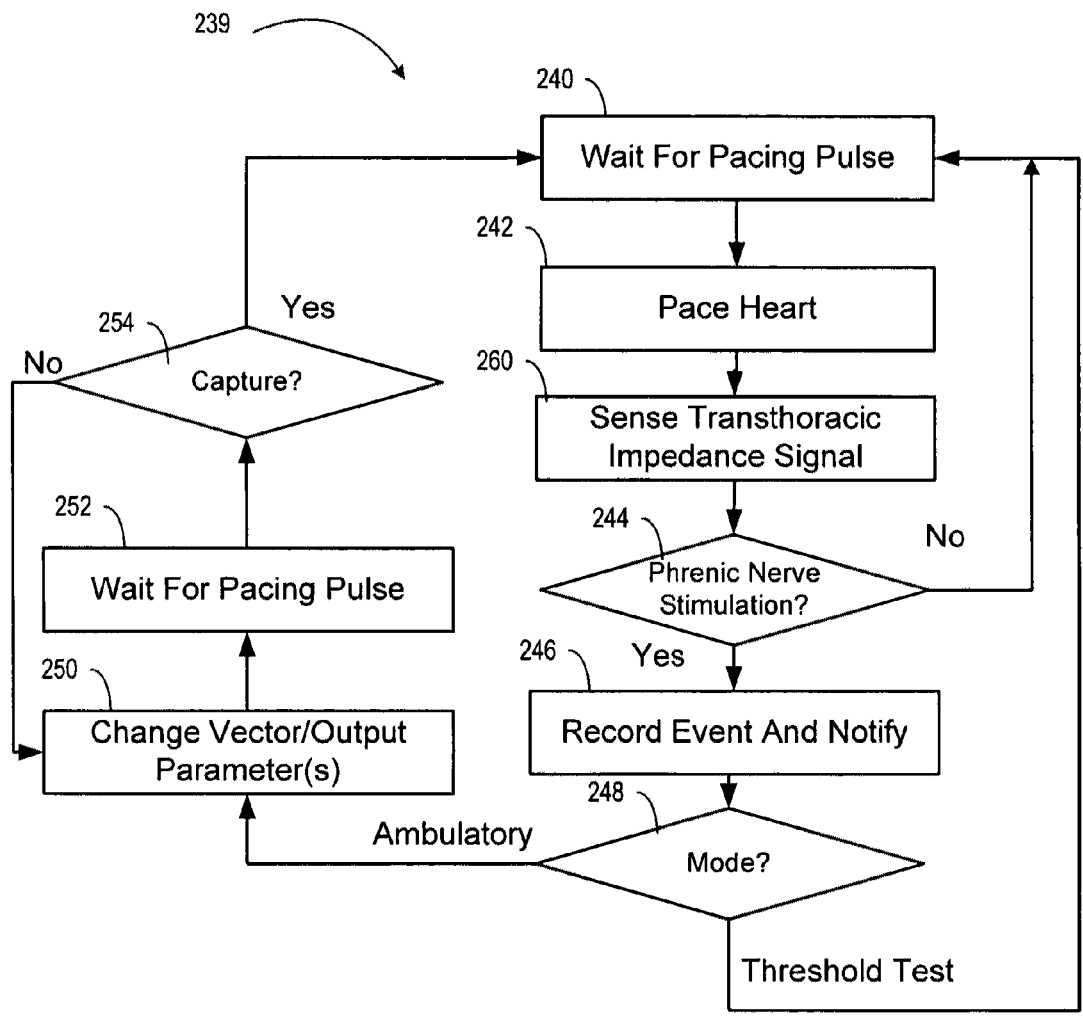
FIG. 5 is a flow chart of another method of reducing phrenic nerve stimulation in accordance with embodiments of the present invention.

FIG. 5 is a flow chart of another method 239 of reducing phrenic nerve stimulation in accordance with embodiments of the present invention. At block 242, the heart is paced at a predetermined rate and amplitude. Transthoracic impedance is sensed 260, and the transthoracic impedance signal is examined to determine if there is diaphragm movement responsive to the cardiac pace. For example, a deviation of the filtered transthoracic impedance signal above a predetermined threshold may be used to identify phrenic nerve stimulation 244. The transthoracic impedance signal may be examined within a time window following each pace pulse for an indication of phrenic stimulation. For example, a window that opens at the left-ventricular pace pulse timing and closes 500 milliseconds after the left-ventricular pace pulse timing may be used to examine the transthoracic impedance signal for a change indicative of phrenic nerve stimulation. In another embodiment, a lock-in amplifier may be used, where the pace signal and transthoracic impedance signal are analyzed for indications of phrenic nerve stimulation.

If no phrenic nerve stimulation is found, a wait 240 occurs until the next scheduled pace pulse. If phrenic nerve stimulation is found, the event 246 may be recorded and/or a notification may occur. For example, the controller of a PIMD may be notified that phrenic nerve stimulation is occurring, and the controller may enter into an optimization algorithm, such as in a command mode, that searches for new vectors, settings, or other controlled parameters that effect capture with a minimum of phrenic nerve stimulation. If a determination 248 is made that the optimization algorithm occurs or is in process by the controller, then the recorded event 246 information is used by the controller, and the method 239 proceeds to the wait 240 for the next pace pulse.

If the determination 248 finds that the PIMD is in ambulatory mode, the PIMD may change 250 a vector, and/or other output parameter(s), wait 252 for the next scheduled pace pulse, and determine 254 if capture occurs at the new setting. For example, the ambulatory mode may simply reduce the pace amplitude at the change 250, and verify that capture still occurs at the reduced level using the determination 254. In alternate embodiments for selecting parameters in ambulatory mode, parameters may be selected from a patient's strength-duration curve that effects cardiac capture and reduces the phrenic nerve stimulation. The PIMD may select pacing pulse width and pacing voltage parameters that lie on a patient's strength-duration curve, to find a set of parameters that reduces and/or minimizes phrenic nerve stimulation. If capture determination 254 is yes after selecting the new parameter(s), then the method 239 returns to the wait 240. If capture determination 254 is no, then another change 250 is made, and the change loop 250, 252, 254 is repeated until a new setting is found that effects capture, before the method 239 continues to the wait 240.

Figure 6:
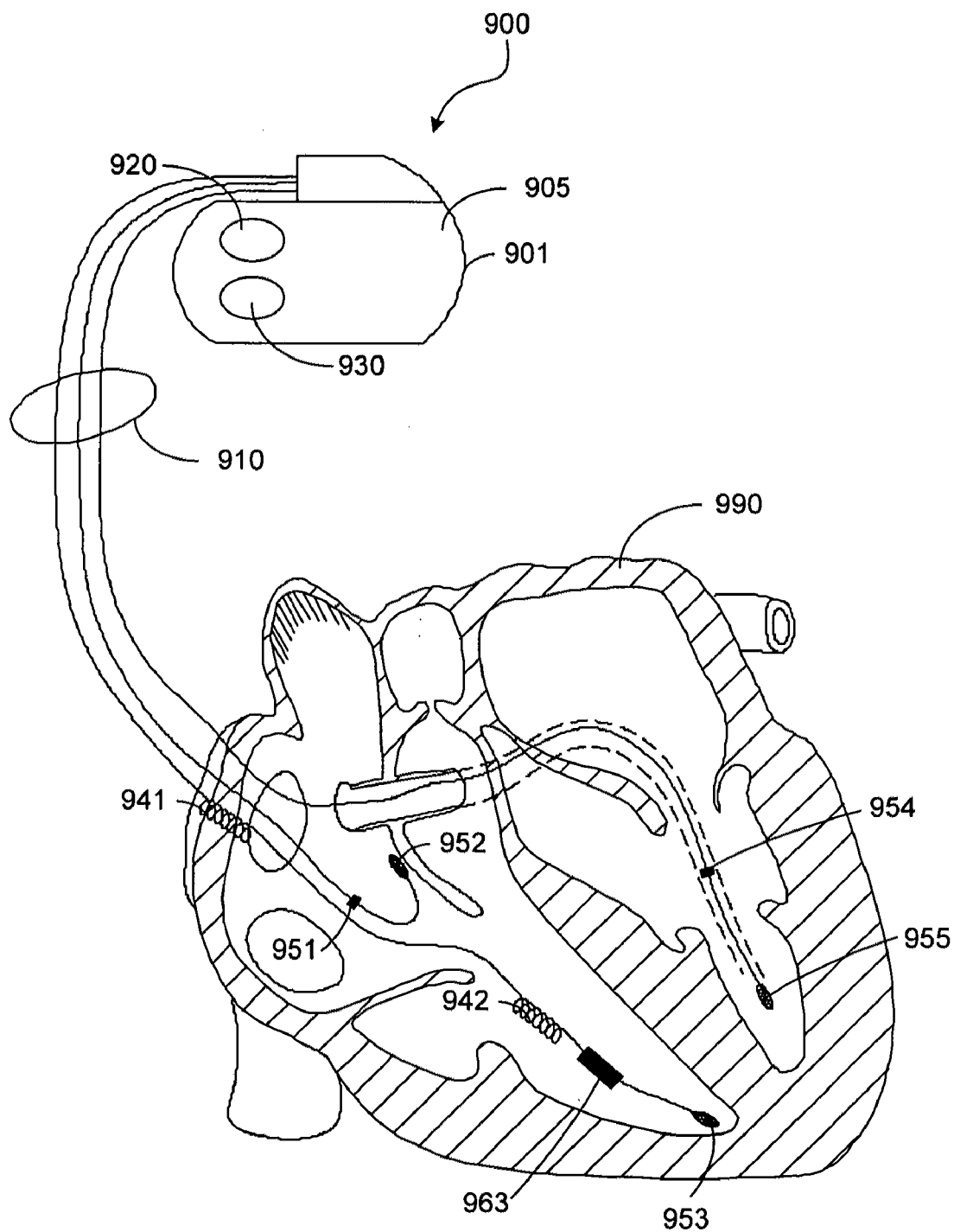
FIG. 6 is an illustration of an implantable cardiac device including a lead assembly shown implanted in a sectional view of a heart, in accordance with embodiments of the invention.

Referring now to FIG. 6, the implantable device illustrated in FIG. 6 is an embodiment of a PIMD implementing phrenic nerve stimulation avoidance methodologies in accordance with the present invention. In this example, the implantable device includes a cardiac rhythm management device (CRM) 900 including an implantable pulse generator 905 electrically and physically coupled to an intracardiac lead system 910.

Portions of the intracardiac lead system 910 are inserted into the patient's heart 990. The intracardiac lead system 910 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 901 of the pulse generator 905 may optionally serve as a can electrode.

Communications circuitry is disposed within the housing 901 for facilitating communication between the pulse generator 905 and an external communication device, such as a portable or bed-side communication station, patient-carried/worn communication station, or external programmer, for example. The communications circuitry may also facilitate unidirectional or bidirectional communication with one or more implanted, external, cutaneous, or subcutaneous physiologic or non-physiologic sensors, patient-input devices and/or information systems.

The pulse generator 905 may optionally incorporate a motion detector 920 that may be used to sense patient activity as well as various respiration and cardiac related conditions. For example, the motion detector 920 may be optionally configured to sense snoring, activity level, and/or chest wall movements associated with respiratory effort, for example. The motion detector 920 may be implemented as an accelerometer positioned in or on the housing 901 of the pulse generator 905. If the motion sensor is implemented as an accelerometer, the motion sensor may also provide respiratory, e.g. rales, coughing, and cardiac, e.g. S1-S4 heart sounds, murmurs, and other acoustic information. Accelerometers may also be used to detect phrenic nerve stimulation, which is further described in commonly owned U.S. Pat. No. 6,772,008, which is hereby incorporated herein by reference.

The lead system 910 and pulse generator 905 of the CRM 900 may incorporate one or more transthoracic impedance sensors that may be used to acquire the patient's respiration waveform, or other respiration-related information. The transthoracic impedance sensor may include, for example, one or more intracardiac electrodes 941, 942, 951-955, 963 positioned in one or more chambers of the heart 990. The intracardiac electrodes 941, 942, 951-955, 963 may be coupled to impedance drive/sense circuitry 930 positioned within the housing of the pulse generator 905.

In one implementation, impedance drive/sense circuitry 930 generates a current that flows through the tissue between an impedance drive electrode 951 and a can electrode on the housing 901 of the pulse generator 905. The voltage at an impedance sense electrode 952 relative to the can electrode changes as the patient's transthoracic impedance changes. The voltage signal developed between the impedance sense electrode 952 and the can electrode is detected by the impedance sense circuitry 930. Other locations and/or combinations of impedance sense and drive electrodes are also possible.

The lead system 910 may include one or more cardiac pace/sense electrodes 951-955 positioned in, on, or about one or more heart chambers for sensing electrical signals from the patient's heart 990 and/or delivering pacing pulses to the heart 990. The intracardiac sense/pace electrodes 951-955, such as those illustrated in FIG. 6, may be used to sense and/or pace one or more chambers of the heart, including the left ventricle, the right ventricle, the left atrium and/or the right atrium. The lead system 910 may include one or more defibrillation electrodes 941, 942 for delivering defibrillation/cardioversion shocks to the heart.

The pulse generator 905 may include circuitry for detecting cardiac arrhythmias and/or for controlling pacing or defibrillation therapy in the form of electrical stimulation pulses or shocks delivered to the heart through the lead system 910. The pulse generator 905 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; 5,916,243; 6,360,127; 6,597,951; and 6,993,389, which are hereby incorporated herein by reference.

Figure 7:
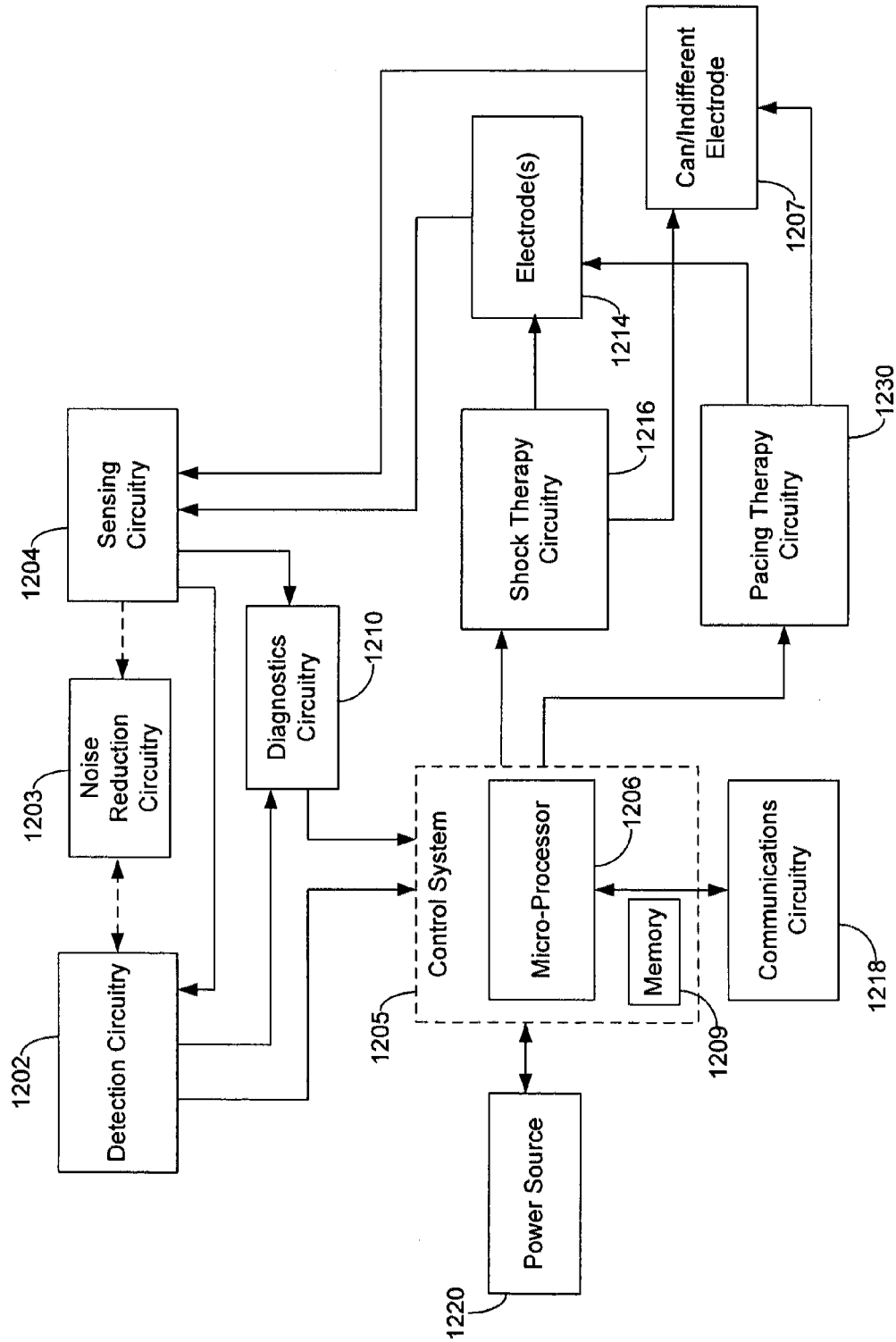
FIG. 7 is a block diagram illustrating various components of an implantable cardiac device in accordance with an embodiment of the present invention.

FIG. 7 is a block diagram depicting various componentry of different arrangements of a PIMD in accordance with embodiments of the present invention. The components, functionality, and configurations depicted in FIG. 7 are intended to provide an understanding of various features and combinations of features that may be incorporated in a PIMD. It is understood that a wide variety of device configurations are contemplated, ranging from relatively sophisticated to relatively simple designs. As such, particular PIMD configurations may include some componentry illustrated in FIG. 7, while excluding other componentry illustrated in FIG. 7.

Illustrated in FIG. 7 is a processor-based control system 1205 which includes a micro-processor 1206 coupled to appropriate memory (volatile and/or non-volatile) 1209, it being understood that any logic-based control architecture may be used. The control system 1205 and associated components provide pacing therapy to the heart. The electrical energy delivered by the PIMD may be in the form of low energy pacing pulses or may also include high-energy pulses for cardioversion or defibrillation.

Cardiac signals are sensed using the electrode(s) 1214 and the can or indifferent electrode 1207 provided on the PIMD housing. Cardiac signals may also be sensed using only the electrode(s) 1214, such as in a non-active can configuration.

As such, unipolar, bipolar, or combined unipolar/bipolar electrode configurations as well as multi-element electrodes and combinations of noise canceling and standard electrodes may be employed. The sensed cardiac signals are received by sensing circuitry 1204, which includes sense amplification circuitry and may also include filtering circuitry and an analog-to-digital (A/D) converter. The sensed cardiac signals processed by the sensing circuitry 1204 may be received by noise reduction circuitry 1203, which may further reduce noise before signals are sent to the detection circuitry 1202.

Noise reduction circuitry 1203 may also be incorporated after sensing circuitry 1204 in cases where high power or computationally intensive noise reduction algorithms are required. The noise reduction circuitry 1203, by way of amplifiers used to perform operations with the electrode signals, may also perform the function of the sensing circuitry 1204. Combining the functions of sensing circuitry 1204 and noise reduction circuitry 1203 may be useful to minimize the necessary componentry and lower the power requirements of the system.

In the illustrative configuration shown in FIG. 7, the detection circuitry 1202 is coupled to, or otherwise incorporates, noise reduction circuitry 1203. The noise reduction circuitry 1203 operates to improve the SNR of sensed cardiac signals by removing noise content of the sensed cardiac signals introduced from various sources. Typical types of cardiac signal noise includes electrical noise and noise produced from skeletal muscles, for example. A number of methodologies for improving the SNR of sensed cardiac signals in the presence of skeletal muscular induced noise, including signal separation techniques incorporating combinations of electrodes and multi-element electrodes, are described hereinbelow.

Detection circuitry 1202 may include a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 1202 to detect and verify the presence and severity of an arrhythmic episode. Examples of arrhythmia detection and discrimination circuitry, structures, and techniques, are disclosed in commonly owned U.S. Pat. Nos. 5,301,677, 6,438,410, and 6,708,058, which are hereby incorporated herein by reference.

The detection circuitry 1202 communicates cardiac signal information to the control system 1205. Memory circuitry 1209 of the control system 1205 contains parameters for operating in various monitoring, pacing, and, if applicable, defibrillation modes, and stores data indicative of cardiac signals received by the detection circuitry 1202. The memory circuitry 1209 may also be configured to store historical EGM and therapy data, which may be used for various purposes and transmitted to an external receiving device as needed or desired.

In certain configurations, the PIMD may include diagnostics circuitry 1210. The diagnostics circuitry 1210 typically receives input signals from the detection circuitry 1202 and the sensing circuitry 1204. The diagnostics circuitry 1210 provides diagnostics data to the control system 1205, it being understood that the control system 1205 may incorporate all or part of the diagnostics circuitry 1210 or its functionality. The control system 1205 may store and use information provided by the diagnostics circuitry 1210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 1205 processes cardiac signal data received from the detection circuitry 1202 and initiates appropriate tachyarrhythmia therapies to terminate cardiac arrhythmic episodes and return the heart to normal sinus rhythm. The control system 1205 is coupled to shock therapy circuitry 1216. The shock therapy circuitry 1216 is coupled to the electrode(s) 1214 and the can or indifferent electrode 1207 of the PIMD housing.

Upon command, the shock therapy circuitry 1216 delivers cardioversion and defibrillation stimulation energy to the heart in accordance with a selected cardioversion or defibrillation therapy. In a less sophisticated configuration, the shock therapy circuitry 1216 is controlled to deliver defibrillation therapies, in contrast to a configuration that provides for delivery of both cardioversion and defibrillation therapies. Examples of PIMD high energy delivery circuitry, structures and functionality, aspects of which may be incorporated in a PIMD of a type that may benefit from aspects of the present invention are disclosed in commonly owned U.S. Pat. Nos. 5,372,606; 5,411,525; 5,468,254; and 5,634,938, which are hereby incorporated herein by reference.

Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference.

As is shown in FIG. 7, the PIMD includes pacing therapy circuitry 1230 that is coupled to the control system 1205 and the electrode(s) 1214 and can/indifferent electrodes 1207. Upon command, the pacing therapy circuitry 1230 delivers pacing pulses to the heart in accordance with a selected pacing therapy.

Control signals, developed in accordance with a pacing regimen by pacemaker circuitry within the control system 1205, are initiated and transmitted to the pacing therapy circuitry 1230 where pacing pulses are generated. A pacing regimen, such as those discussed and incorporated herein, may be modified by the control system 1205. In one particular application, a phrenic nerve stimulation avoidance methodology of the present invention may be implemented to enhance capture detection and/or capture threshold determinations, such as by selecting an optimal vector for sensing an evoked response resulting from application of a capture pacing stimulus that does not cause phrenic nerve stimulation.

The PIMD shown in FIG. 7 may be configured to receive signals from one or more physiologic and/or non-physiologic sensors. Depending on the type of sensor employed, signals generated by the sensors may be communicated to transducer circuitry coupled directly to the detection circuitry 1202 or indirectly via the sensing circuitry 1204. It is noted that certain sensors may transmit sense data to the control system 1205 without processing by the detection circuitry 1202.

Communications circuitry 1218 is coupled to the microprocessor 1206 of the control system 1205. The communications circuitry 1218 allows the PIMD to communicate with one or more receiving devices or systems situated external to the PIMD. By way of example, the PIMD may communicate with a patient-worn, portable or bedside communication system via the communications circuitry 1218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the PIMD via the communications circuitry 1218. It is noted that physiologic or non-physiologic sensors equipped with wireless transmitters or transceivers may communicate with a receiving system external of the patient.

The communications circuitry 1218 allows the PIMD to communicate with an external programmer and/or advanced patient management device. In one configuration, the communications circuitry 1218 and the programmer unit (not shown) use a wire loop antenna and a radio frequency telemetric link, as is known in the art, to receive and transmit signals and data between the programmer unit and communications circuitry 1218. In this manner, programming commands and data are transferred between the PIMD and the programmer unit during and after implant. Using a programmer, a physician is able to set or modify various parameters used by the PIMD. For example, a physician may set or modify parameters affecting monitoring, detection, pacing, and defibrillation functions of the PIMD, including pacing and cardioversion/defibrillation therapy modes. The programmer and/or advanced patient management device may include a signal processor to process signals and implement phrenic nerve stimulation reduction algorithms and processes in accordance with the present invention.

Typically, the PIMD is encased and hermetically sealed in a housing suitable for implanting in a human body as is known in the art. Power to the PIMD is supplied by an electrochemical power source 1220 housed within the PIMD. In one configuration, the power source 1220 includes a rechargeable battery. According to this configuration, charging circuitry is coupled to the power source 1220 to facilitate repeated non-invasive charging of the power source 1220. The communications circuitry 1218, or separate receiver circuitry, is configured to receive RF energy transmitted by an external RF energy transmitter. The PIMD may, in addition to a rechargeable power source, include a non-rechargeable battery. It is understood that a rechargeable power source need not be used, in which case a long-life non-rechargeable battery is employed.

The detection circuitry 1202, which is coupled to a microprocessor 1206, may be configured to incorporate, or communicate with, specialized circuitry for processing sensed signals in manners particularly useful in a cardiac sensing and/or stimulation device that includes phrenic nerve stimulation reduction. As is shown by way of example in FIG. 7, the detection circuitry 1202 may receive information from multiple physiologic and non-physiologic sensors.

Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical device, comprising:
   a plurality of electrodes electrically coupled to a heart;
   a pulse generator coupled to the plurality of electrodes and configured to sense cardiac activity and deliver pacing pulses to a heart using at least some of the plurality of electrodes;
   a transthoracic impedance sensor configured to sense a transthoracic impedance signal; and
   a control circuit coupled to the pulse generator and the transthoracic impedance sensor, the control circuit configured to detect a breathing event based on a temporal association between pacing pulse delivery during a non-refractory period of the heart and a perturbation in the transthoracic impedance signal, the control circuit further configured to verify that the detected breathing event is representative of phrenic nerve stimulation resulting from pacing pulse delivery based on detection of an additional perturbation in the transthoracic impedance signal that is temporally associated with an additional pacing pulse delivered during a cardiac refractory period of the heart.

2. The device of claim 1, wherein the control circuit is configured to detect the breathing event and verify that the breathing event is representative of phrenic nerve stimulation based on detection of one or both of inspiration and expiration corresponding to pacing pulse delivery timing.

3. The device of claim 1, wherein the control circuit is configured to detect the breathing event and verify that the breathing event is representative of phrenic nerve stimulation based on detection of a change in one or both of inspiration and expiration superimposed over a normal breathing pattern, where the change corresponds with pacing pulse delivery timing.

4. The device of claim 1, wherein the control circuit is configured to open a time window following delivery of each pacing pulse, and evaluate the transthoracic impedance signal during the time window for the perturbation indicative of phrenic nerve stimulation.

5. The device of claim 4, wherein the control circuit is configured to open the time window following delivery of a left-ventricular pacing pulse and close the time window after expiration of a predetermined period following left-ventricular pacing pulse delivery.

6. The device of claim 1, wherein the control circuit is configured to alter one or more of a pacing vector, pacing pulse amplitude, and pacing pulse width to reduce the phrenic nerve stimulation.

7. The device of claim 1, wherein the control circuit is configured to search for one or more of new pacing vectors, pacing parameter settings, and pulse generator control parameters that effect capture with reduced phrenic nerve stimulation.

8. The device of claim 1, wherein the control circuit is configured, in response to determining that the device is in an ambulatory mode, to change a pacing vector or one or more pacing parameters, wait for the next scheduled pacing pulse to be delivered, and determine if capture occurs using the changed pacing vector or the one or more changed pacing parameters.

9. The device of claim 1, wherein the control circuit is configured, in response to determining that the device is in an ambulatory mode, to adjust one or more pacing parameters from a strength-duration curve established for a patient that effects cardiac capture and reduces phrenic nerve stimulation.

10. The device of claim 1, wherein the control circuit comprises a band-pass filter centered at a pacing rate and coupled to an output of the transthoracic impedance sensor, the filter configured to detect the perturbation in the transthoracic impedance signal indicative of phrenic nerve stimulation.

11. The device of claim 1, wherein the control circuit comprises a lock-in amplifier configured to analyze the pacing pulses and the transthoracic impedance signal for indications of phrenic nerve stimulation.

12. The device of claim 1, wherein the control circuit is configured to verify that the detected breathing event is representative of phrenic nerve stimulation resulting from pacing pulse delivery independent of cardiac motion.

13. The device of claim 1, wherein a signal processor is provided in a patient-external device or system, the signal processor and the control circuit coupled to respective communication devices to facilitate wireless communication between the signal processor and the control circuit.

14. The device of claim 1, wherein a signal processor is provided in a network server system, the signal processor and the control circuit coupled to respective communication devices to facilitate wireless communication between the signal processor and the control circuit.

15. A medical device, comprising:
a plurality of electrodes electrically coupled to a heart;
a pulse generator coupled to the plurality of electrodes and configured to sense cardiac activity and deliver pacing pulses to a heart using at least some of the plurality of electrodes;
a transthoracic impedance sensor configured to sense a transthoracic impedance signal; and
a control circuit coupled to the pulse generator and the transthoracic impedance sensor, the control circuit configured to detect a breathing event based on a temporal association between pacing pulse delivery during a non-refractory period of the heart and a perturbation in the transthoracic impedance signal, the control circuit further configured to verify that the detected breathing event is representative of phrenic nerve stimulation resulting from pacing pulse delivery based on detection of an additional perturbation in the transthoracic impedance signal that is temporally associated with an additional delivered pacing pulse.

16. The device of claim 15, wherein the control circuit is configured to detect the breathing event and verify that the breathing event is representative of phrenic nerve stimulation based on detection of one or both of inspiration and expiration corresponding to pacing pulse delivery timing.

17. The device of claim 15, wherein the control circuit is configured to detect the breathing event and verify that the breathing event is representative of phrenic nerve stimulation based on detection of a change in one or both of inspiration and expiration superimposed over a normal breathing pattern, where the change corresponds with pacing pulse delivery timing.

18. The device of claim 15, wherein the control circuit is configured to open a time window following delivery of each pacing pulse, and evaluate the transthoracic impedance signal during the time window for the perturbation indicative of phrenic nerve stimulation.

19. The device of claim 18, wherein the control circuit is configured to open the time window following delivery of a left-ventricular pacing pulse and close the time window after expiration of a predetermined period following left-ventricular pacing pulse delivery.

20. The device of claim 15, wherein the control circuit is configured to alter one or more of a pacing vector, pacing pulse amplitude, and pacing pulse width to reduce the phrenic nerve stimulation.

21. The device of claim 15, wherein the control circuit is configured to search for one or more of new pacing vectors, pacing parameter settings, and pulse generator control parameters that effect capture with reduced phrenic nerve stimulation.

22. The device of claim 15, wherein the control circuit is configured, in response to determining that the device is in an ambulatory mode, to change a pacing vector or one or more pacing parameters, wait for the next scheduled pacing pulse to be delivered, and determine if capture occurs using the changed pacing vector or the one or more changed pacing parameters.

23. The device of claim 15, wherein the control circuit is configured, in response to determining that the device is in an ambulatory mode, to adjust one or more pacing parameters from a strength-duration curve established for a patient that effects cardiac capture and reduces phrenic nerve stimulation.

24. The device of claim 15, wherein the control circuit comprises a band-pass filter centered at a pacing rate and coupled to an output of the transthoracic impedance sensor, the filter configured to detect the perturbation in the transthoracic impedance signal indicative of phrenic nerve stimulation.

25. The device of claim 15, wherein the control circuit comprises a lock-in amplifier configured to analyze the pacing pulses and the transthoracic impedance signal for indications of phrenic nerve stimulation.

26. The device of claim 15, wherein the control circuit is configured to verify that the detected breathing event is representative of phrenic nerve stimulation resulting from pacing pulse delivery independent of cardiac motion.

27. The device of claim 15, wherein a signal processor is provided in a patient-external device or system, the signal processor and the control circuit coupled to respective communication devices to facilitate wireless communication between the signal processor and the control circuit.

28. The device of claim 15, wherein a signal processor is provided in a network server system, the signal processor and the control circuit coupled to respective communication devices to facilitate wireless communication between the signal processor and the control circuit.

* * * * *